(12) United States Patent
Matsunaga et al.

(10) Patent No.: US 10,729,408 B2
(45) Date of Patent: Aug. 4, 2020

(54) ULTRASOUND DIAGNOSIS APPARATUS AND CONTROLLING METHOD

(71) Applicant: Toshiba Medical Systems Corporation, Otawara-shi (JP)

(72) Inventors: Satoshi Matsunaga, Nasushiobara (JP); Kazutoshi Sadamitsu, Otawara (JP); Osamu Nakajima, Otawara (JP); Tomokazu Fujii, Nasushiobara (JP); Masaki Watanabe, Shioya (JP)

(73) Assignee: Canon Medical Systems Corporation, Otawara-shi (JP)

( * ) Notice: Subject to any disclaimer, the term of this patent is extended or adjusted under 35 U.S.C. 154(b) by 683 days.

(21) Appl. No.: 14/856,894

(22) Filed: Sep. 17, 2015

(65) Prior Publication Data
US 2016/0000408 A1   Jan. 7, 2016

Related U.S. Application Data

(63) Continuation of application No. PCT/JP2014/058114, filed on Mar. 24, 2014.

(30) Foreign Application Priority Data

Mar. 22, 2013   (JP) .................................. 2013-059793

(51) Int. Cl.
*A61B 8/08*   (2006.01)
*A61B 8/06*   (2006.01)
(Continued)

(52) U.S. Cl.
CPC .............. *A61B 8/5207* (2013.01); *A61B 8/06* (2013.01); *A61B 8/0891* (2013.01); *A61B 8/14* (2013.01);
(Continued)

(58) Field of Classification Search
CPC ....... A61B 8/06; A61B 8/0891; A61B 8/4245; A61B 8/483; A61B 8/466; A61B 8/488;
(Continued)

(56) References Cited

U.S. PATENT DOCUMENTS 5,329,929 A * 7/1994 Sato .......................... A61B 8/06
                                                                    128/916
6,132,379 A * 10/2000 Patacsil ..................... A61B 8/06
                                                                    600/459
(Continued)

FOREIGN PATENT DOCUMENTS

JP   05-137728 A    6/1993
JP   07-178091 A    7/1995
(Continued)

OTHER PUBLICATIONS

Frank Lindseth, Ultrasound Guided Surgery: Multimodal Visualization and Navigation Accuracy, Norwegian University of Science and Technology, Dec. 2002.*
(Continued)

*Primary Examiner* — Bo Joseph Peng
(74) *Attorney, Agent, or Firm* — Oblon, McClelland, Maier & Neustadt, L.L.P.

(57) ABSTRACT

An ultrasound diagnosis apparatus according to an embodiment includes index image data generating circuitry and controlling circuitry. The index image data generating circuitry is configured to generate index image data indicating a relative positional relationship between extending direction information and information indicating a scanned position by an ultrasound wave transmitted from an ultrasound probe, wherein the extending direction information indicates a blood vessel extending direction and is generated on a basis of volume data representing a three-dimensional region that includes at least a part of the blood vessel region of a subject. The controlling circuitry is configured to cause a monitor to display the index image data.

19 Claims, 18 Drawing Sheets

(51) Int. Cl.
*A61B 8/00* (2006.01)
*A61B 8/14* (2006.01)
*A61B 6/00* (2006.01)

(52) U.S. Cl.
CPC .......... *A61B 8/4245* (2013.01); *A61B 8/4254* (2013.01); *A61B 8/463* (2013.01); *A61B 8/466* (2013.01); *A61B 8/483* (2013.01); *A61B 8/488* (2013.01); *A61B 8/5223* (2013.01); *A61B 8/5261* (2013.01); *A61B 8/54* (2013.01); *A61B 6/5247* (2013.01)

(58) Field of Classification Search
CPC ....... A61B 8/5261; A61B 8/14; A61B 8/4254; A61B 8/463; A61B 8/5207; A61B 8/5223; A61B 8/54; A61B 6/5247
See application file for complete search history.

(56) References Cited

U.S. PATENT DOCUMENTS

| | | | |
|---|---|---|---|
| 2007/0146242 A1* | 6/2007 | Miller | G09G 3/2074 345/76 |
| 2009/0024029 A1 | 1/2009 | Murashita | |
| 2009/0030321 A1 | 1/2009 | Baba et al. | |
| 2011/0196237 A1* | 8/2011 | Pelissier | A61B 8/06 600/454 |
| 2011/0246129 A1 | 10/2011 | Ishikawa et al. | |
| 2012/0177276 A1 | 7/2012 | Migita et al. | |
| 2012/0296214 A1 | 11/2012 | Urabe et al. | |

FOREIGN PATENT DOCUMENTS

| | | |
|---|---|---|
| JP | 09-122126 A | 5/1997 |
| JP | 2004-229823 A | 8/2004 |
| JP | 2008-148858 A | 7/2008 |
| JP | 2009-022342 A | 2/2009 |
| JP | 2009-028083 A | 2/2009 |
| JP | 2009-056125 A | 3/2009 |
| JP | 2010-279486 A | 12/2010 |
| WO | WO 2011/033793 A1 | 3/2011 |
| WO | WO 2011/074271 A1 | 6/2011 |

OTHER PUBLICATIONS

International Search Report dated May 13, 2014 in PCT/JP2014/058114 filed Mar. 24, 2014 with English translation.
Written Opinion dated May 13, 2014 in PCT/JP2014/058114 filed Mar. 24, 2014.

* cited by examiner

ULTRASOUND DIAGNOSIS APPARATUS AND CONTROLLING METHOD

CROSS-REFERENCE TO RELATED APPLICATIONS

This application is a continuation of PCT international application Ser. No. PCT/JP2014/058114 filed on Mar. 24, 2014 which designates the United States, incorporated herein by reference, and which claims the benefit of priority from Japanese Patent Application No. 2013-059793, filed on Mar. 22, 2013, the entire contents of which are incorporated herein by reference.

FIELD

Embodiments described herein relate generally to an ultrasound diagnosis apparatus and a controlling method.

BACKGROUND

Ultrasound diagnosis apparatuses may be used for diagnosing stenoses in blood vessels. For example, an ultrasound diagnosis apparatus obtains blood flow information by using a color Doppler mode or a pulse Doppler mode. Blood flow rates, which serve as a type of blood flow information, become faster and slower repeatedly at regular intervals. For example, medical doctors and the like make a diagnosis as to whether a stenosis has occurred in a blood vessel or not by comparing the ratio between the largest value and the smallest value among obtained blood flow rate values with a reference value.

Further, to improve the precision level of the diagnosis, it is necessary to obtain accurate blood flow information. To obtain accurate blood flow information, for example, it is desirable to arrange the angle (expressed as θ degrees) formed by the transmission direction of an ultrasound beam transmitted from an ultrasound probe and the direction in which the blood vessel extends (hereinafter, "blood vessel extending direction") so as to be an angle desired by the operator.

DETAILED DESCRIPTION

Exemplary embodiments of an ultrasound diagnosis apparatus and a controlling method will be explained below, with reference to the accompanying drawings.

An ultrasound diagnosis apparatus according to an embodiment includes index image data generating circuitry and controlling circuitry. The index image data generating circuitry is configured to generate index image data indicating a relative positional relationship between extending direction information and information indicating a scanned position by an ultrasound wave transmitted from an ultrasound probe, wherein the extending direction information indicates a blood vessel extending direction and is generated on a basis of volume data representing a three-dimensional region that includes at least a part of the blood vessel region of a subject. The controlling circuitry is configured to cause a monitor to display the index image data.

First Embodiment

Figure 1:
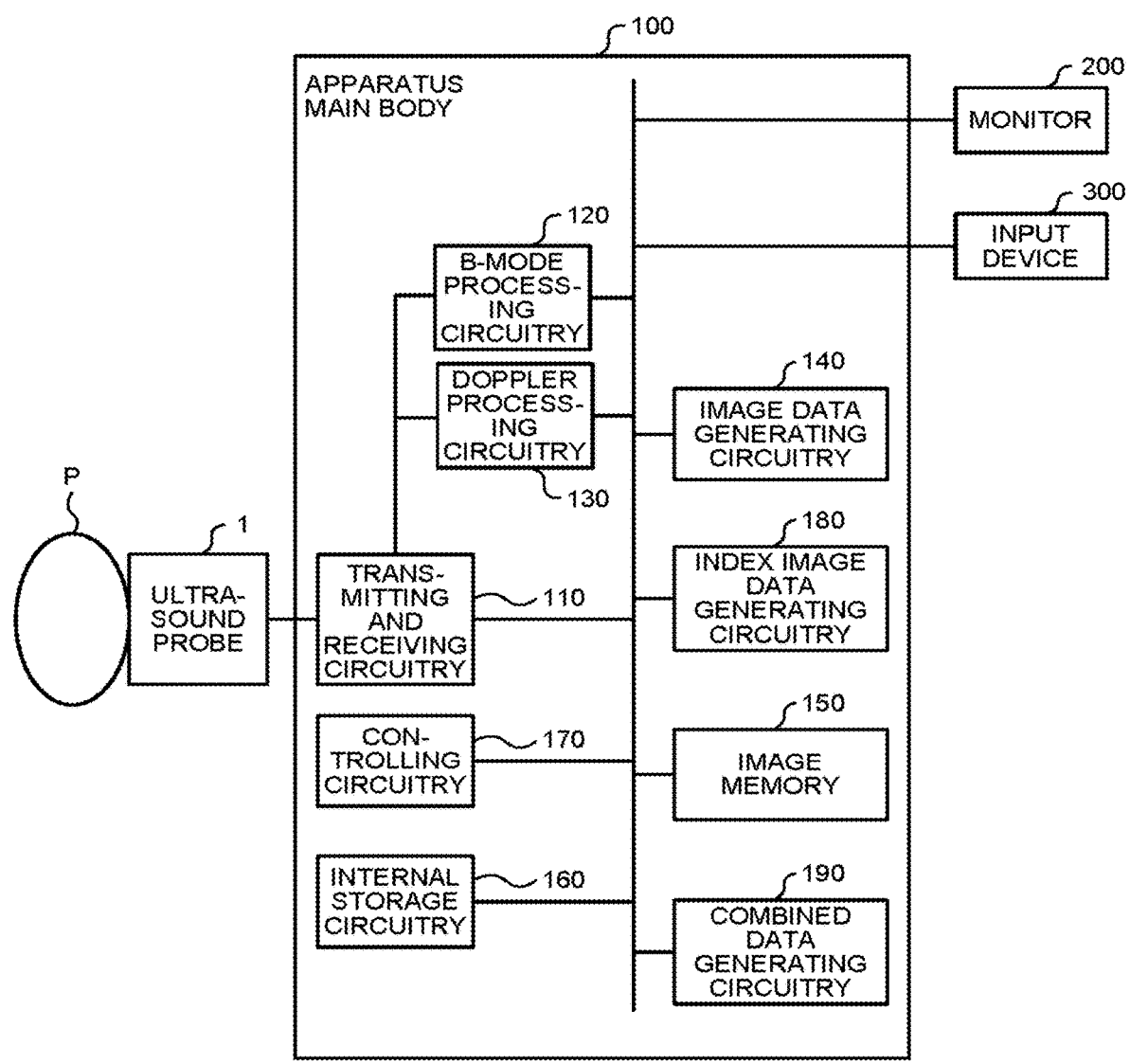
FIG. 1 is a block diagram of an exemplary configuration of an ultrasound diagnosis apparatus according to a first embodiment.

To begin with, a configuration of an ultrasound diagnosis apparatus according to a first embodiment will be explained. FIG. 1 is a block diagram of an exemplary configuration of the ultrasound diagnosis apparatus according to the first embodiment. As illustrated in FIG. 1, the ultrasound diagnosis apparatus according to the first embodiment includes an ultrasound probe 1, an apparatus main body 100, a monitor 200, and an input device 300.

The ultrasound probe 1 includes a plurality of piezoelectric transducer elements, which generate an ultrasound wave on the basis of a drive signal supplied from transmitting and receiving circuitry 110 included in the apparatus main body 100 (explained later). Further, the plurality of piezoelectric transducer elements included in the ultrasound probe 1 are configured to receive a reflected wave from an examined subject P and to convert the received reflected wave into an electric signal. Further, the ultrasound probe 1 includes matching layers provided for the piezoelectric transducer elements, as well as a backing member that prevents ultrasound waves from propagating rearward from the piezoelectric transducer elements. The ultrasound probe 1 is detachably connected to the apparatus main body 100. In the first embodiment, an example will be explained in which the ultrasound probe 1 is a probe (a 2D array probe) that includes the plurality of piezoelectric transducer elements arranged in a two-dimensional formation.

When an ultrasound wave is transmitted from the ultrasound probe 1 to the subject P, the transmitted ultrasound wave is repeatedly reflected on a surface of discontinuity of acoustic impedances at a tissue in the body of the subject P and is received as a reflected-wave signal by the plurality of piezoelectric transducer elements included in the ultrasound probe 1. The amplitude of the received reflected-wave signal is dependent on the difference between the acoustic impedances on the surface of discontinuity on which the ultrasound wave is reflected. When the transmitted ultrasound pulse is reflected on the surface of a moving blood flow, a cardiac wall, or the like, the reflected-wave signal is, due to the Doppler effect, subject to a frequency shift, depending on a velocity component of the moving members with respect to the ultrasound wave transmission direction.

For example, in the first embodiment, the ultrasound probe 1 is a mechanical 4D probe or a 2D array probe that scans the subject P three-dimensionally.

The input device 300 includes a mouse, a keyboard, a button, a panel switch, a touch command screen, a foot switch, a trackball, a joystick, and the like. The input device 300 is configured to receive various types of setting requests from an operator of the ultrasound diagnosis apparatus and to transfer the received various types of setting requests to the apparatus main body 100.

The monitor 200 is configured to display a Graphical User Interface (GUI) used by the operator of the ultrasound diagnosis apparatus to input the various types of setting requests through the input device 300 and to display ultrasound image data and the like generated by the apparatus main body 100.

The apparatus main body 100 is configured to generate the ultrasound image data on the basis of the reflected-wave signal received by the ultrasound probe 1. The apparatus main body 100 illustrated in FIG. 1 is capable of generating two-dimensional ultrasound image data on the basis of two-dimensional reflected-wave signals and is capable of generating three-dimensional ultrasound image data on the basis of three-dimensional reflected-wave signals.

As illustrated in FIG. 1, the apparatus main body 100 includes the transmitting and receiving circuitry 110, B-mode processing circuitry 120, Doppler processing circuitry 130, image data generating circuitry 140, image memory 150, internal storage circuitry 160, controlling circuitry 170, index image data generating circuitry 180, and combined data generating circuitry 190.

The transmitting and receiving circuitry 110 is configured to control the ultrasound transmissions and receptions on the basis of an instruction from the controlling circuitry 170 (explained later). The transmitting and receiving circuitry 110 includes a pulse generator, transmission delaying circuitry, a pulser, and the like and is configured to supply the drive signal to the ultrasound probe 1. The pulse generator repeatedly generates a rate pulse for forming a transmission ultrasound wave at a predetermined rate frequency. Further, the transmission delaying circuitry applies a delay period that is required to converge the ultrasound wave generated by the ultrasound probe 1 into the form of a beam and to determine transmission directionality and that corresponds to each of the piezoelectric transducer elements, to each of the rate pulses generated by the pulse generator. Further, the pulser applies the drive signal (a drive pulse) to the ultrasound probe 1 with timing based on the rate pulses.

In other words, the transmission delaying circuitry arbitrarily adjusts the transmission directions of the ultrasound waves transmitted from the piezoelectric transducer element surfaces, by varying the delay periods applied to the rate pulses. Further, the transmission delaying circuitry controls the position of a converged point (a transmission focus) in the depth direction of the ultrasound wave transmissions, by varying the delay periods applied to the rate pulses.

The transmitting and receiving circuitry 110 has a function to be able to instantly change the transmission frequency, the transmission drive voltage, and the like, for the purpose of executing a predetermined scanning sequence on the basis of an instruction from the controlling circuitry 170 (explained later). In particular, the configuration to change the transmission drive voltage is realized by using a linear-amplifier-type transmitting circuit of which the value can be instantly switched or by using a mechanism configured to electrically switch between a plurality of power sources.

Further, the transmitting and receiving circuitry 110 includes an amplifying circuit, an Analog/Digital (A/D) converter, a reception delaying circuit, an adder, a quadrature detection circuit, and the like and is configured to generate reflected-wave data by performing various types of processes on the reflected-wave signal received by the ultrasound probe 1. The amplifying circuit performs a gain correction process by amplifying the reflected-wave signal for each of channels. The A/D converter applies an A/D conversion to the gain-corrected reflected-wave signals. The reception delaying circuit applies a reception delay period required to determine reception directionality to the digital data. The adder performs an adding process on the reflected-wave signals to which the reception delay period has been applied by the reception delaying circuit. As a result of the adding process performed by the adder, reflected components from the direction corresponding to the reception directionality of the reflected-wave signals are emphasized. Further, the quadrature detection circuit converts an output signal from the adder into an In-phase signal (an I signal) and a Quadrature-phase signal (a Q signal) in a baseband. Further, the quadrature detection circuit stores the I signal and the Q signal (hereinafter, "IQ signals") into a frame buffer (not illustrated) as the reflected-wave data. Alternatively, the quadrature detection circuit may convert the output signal from the adder into a Radio Frequency (RF) signal and store the RF signal into a frame buffer (not illustrated).

When the subject P is two-dimensionally scanned, the transmitting and receiving circuitry 110 causes the ultrasound probe 1 to transmit a two-dimensional ultrasound wave. Further, the transmitting and receiving circuitry 110 generates two-dimensional reflected-wave data from the two-dimensional reflected-wave signals received by the ultrasound probe 1. In another example, when the subject P is three-dimensionally scanned, the transmitting and receiving circuitry 110 causes the ultrasound probe 1 to transmit a three-dimensional ultrasound wave. Further, the transmitting and receiving circuitry 110 generates three-dimensional reflected-wave data from the three-dimensional reflected-wave signals received by the ultrasound probe 1.

The B-mode processing circuitry 120 and the Doppler processing circuitry 130 are processing circuitry configured to perform various types of signal processing processes on the reflected-wave data generated by the transmitting and receiving circuitry 110 from the reflected-wave signals. The B-mode processing circuitry 120 is configured to receive the reflected-wave data from the transmitting and receiving circuitry 110 and to generate data (B-mode data) in which the strength of each signal is expressed by a degree of brightness, by performing a logarithmic amplification, an envelope detection process, and the like on the received reflected-wave data. Further, the Doppler processing circuitry 130 is configured to detect a Doppler shift by performing a frequency analysis on the reflected-wave data received from the transmitting and receiving circuitry 110 and to generate information (Doppler data) about moving members in the subject's body, on the basis of detection results. In this situation, examples of the moving members include, for example, blood flows, tissues such as the cardiac wall, and a contrast agent. For example, the Doppler processing circuitry 130 has a function (the pulse Doppler mode) of displaying a waveform image based on a detection result of the Doppler shift corresponding to one or more measuring positions in the subject's body and a function (the color Doppler mode) of displaying a color image based on a detection result of the Doppler shift corresponding to a plurality of measuring positions in a predetermined region in the subject's body. The B-mode processing circuitry 120 and the Doppler processing circuitry 130 obtain the reflected-wave data via the frame buffer mentioned above.

The B-mode processing circuitry 120 and the Doppler processing circuitry 130 illustrated in FIG. 1 are able to process both reflected-wave data corresponding to a plurality positions within a two-dimensional space and reflected-wave data corresponding to a plurality of positions within a three-dimensional space. In other words, the B-mode processing circuitry 120 is able to generate B-mode data corresponding to the plurality of positions within the two-dimensional space from the reflected-wave data corresponding to the plurality of positions within the two-dimensional space and is also able to generate B-mode data corresponding to the plurality of positions within the three-dimensional space from the reflected-wave data corresponding to the plurality of positions within the three-dimensional space. Further, the Doppler processing circuitry 130 is able to generate Doppler data corresponding to the plurality of positions within the two-dimensional space from the reflected-wave data corresponding to the plurality of positions within the two-dimensional space and is also able to generate Doppler data corresponding to the plurality of positions within the three-dimensional space from the reflected-wave data corresponding to the plurality of positions within the three-dimensional space.

The image data generating circuitry 140 is configured to generate ultrasound image data from the data generated by the B-mode processing circuitry 120 and the Doppler processing circuitry 130. The image data generating circuitry 140 generates display-purpose two-dimensional B-mode image data from the B-mode data that corresponds to the plurality of positions within the two-dimensional space and that is generated by the B-mode processing circuitry 120. Further, the image data generating circuitry 140 generates display-purpose two-dimensional Doppler image data from the Doppler data that corresponds to the plurality of positions within the two-dimensional space and that is generated by the Doppler processing circuitry 130. The two-dimensional Doppler image data is velocity image data, dispersion image data, power image data, or image data combining any of these types of image data.

In this situation, generally speaking, the image data generating circuitry 140 converts (by performing a scan convert process) a scanning line signal sequence from an ultrasound scan into a scanning line signal sequence in a video format used by, for example, television and generates display-purpose ultrasound image data. More specifically, the image data generating circuitry 140 generates the display-purpose ultrasound image data by performing a coordinate transformation process compliant with the ultrasound scanning mode used by the ultrasound probe 1. Further, besides the scan convert process, the image data generating circuitry 140 performs, as various types of image processing processes, for example, an image processing process (a smoothing process) to re-generate an average-brightness-value image, an image processing process (an edge enhancement process) that employs a differential filter within the image, and the like, by using a plurality of image frames that are available after the scan convert process. Further, the image data generating circuitry 140 combines text information of various parameters, scale graduations, body marks, and the like with the ultrasound image data.

The B-mode data and the Doppler data are each ultrasound image data before the scan covert process, whereas the data generated by the image data generating circuitry 140 is display-purpose ultrasound image data after the scan covert process. The B-mode data and the Doppler data may each be referred to as "raw data". The image data generating circuitry 140 generates display-purpose two-dimensional ultrasound image data from the two-dimensional ultrasound image data before the scan convert process.

Further, the image data generating circuitry 140 generates display-purpose three-dimensional B-mode image data by performing a coordinate transformation process on the B-mode data that corresponds to the plurality of positions within the three-dimensional space and that is generated by the B-mode processing circuitry 120. Further, the image data generating circuitry 140 generates display-purpose three-dimensional Doppler image data by performing a coordinate transformation process on the Doppler data that corresponds to the plurality of positions within the three-dimensional space and that is generated by the Doppler processing circuitry 130. The "three-dimensional B-mode image data and three-dimensional Doppler image data" may be referred to as "three-dimensional ultrasound image data (volume data)".

Further, the image data generating circuitry 140 performs various types of rendering processes on the volume data, for the purpose of generating two-dimensional data used for displaying the volume data on the monitor 200. Examples of the rendering processes performed by the image data generating circuitry 140 include a process to generate Multi Planar Reconstruction (MPR) image data from the volume data by implementing an MPR method. Another example of the rendering processes performed by the image data generating circuitry 140 is a Volume Rendering (VR) process to generate two-dimensional image data reflecting three-dimensional information.

The image memory 150 is a memory configured to store therein the display-purpose image data generated by the image data generating circuitry 140. Further, the image memory 150 is also capable of storing therein the data generated by the B-mode processing circuitry 120 and the Doppler processing circuitry 130. The data generated by the Doppler processing circuitry 130 includes blood flow information. After a diagnosis process, for example, the operator is able to invoke the B-mode data and the Doppler data stored in the image memory 150. The invoked data serves as the display-purpose ultrasound image data after being routed through the image data generating circuitry 140. Also, the image memory 150 stores therein information in which a scanned position in a blood vessel is kept in correspondence with blood flow information at the scanned position. The scanned position may include information about the angle of a scanning line with respect to the blood vessel extending direction, corresponding to the time when the blood flow information is obtained. Further, the image memory 150 also stores therein the volume data generated by the image data generating circuitry 140. Further, the image memory 150 is also capable of storing therein the reflected-wave data output by the transmitting and receiving circuitry 110.

The internal storage circuitry 160 is configured to store therein control computer programs (hereinafter, "control programs") to realize the ultrasound transmissions and receptions, image processing, and display processing, as well as various types of data such as diagnosis information (e.g., subjects' IDs, medical doctors' observations), diagnosis protocols, and various types of body marks. Further, the internal storage circuitry 160 may be used, as necessary, for storing therein any of the image data stored in the image memory 150. Further, it is possible to transfer the data stored in the internal storage circuitry 160 to an external apparatus via an interface (not illustrated). Further, the internal storage circuitry 160 is also capable of storing therein data transferred thereto from an external apparatus via an interface (not illustrated).

The controlling circuitry 170 is configured to control the overall processes performed by the ultrasound diagnosis apparatus. More specifically, on the basis of the various types of setting requests input by the operator via the input device 300 and the various types of control programs and the various types of data read from the internal storage circuitry 160, the controlling circuitry 170 controls processes performed by the transmitting and receiving circuitry 110, the B-mode processing circuitry 120, the Doppler processing circuitry 130, and the image data generating circuitry 140. Further, the controlling circuitry 170 exercises control so that the monitor 200 displays the display-purpose ultrasound image data stored in the image memory 150 and the internal storage circuitry 160. Further, the controlling circuitry 170 causes index image data generated by the index image data generating circuitry 180 (explained later) to be displayed in a part of the area of the monitor 200. Further, the controlling circuitry 170 causes the monitor 200 to display combined data generated by the combined data generating circuitry 190 (explained later).

The index image data generating circuitry 180 is configured to generate the index image data indicating a relative positional relationship between extending direction information and information indicating a scanned position by an ultrasound wave transmitted from the ultrasound probe 1, wherein the extending direction information indicates a blood vessel extending direction and is generated on a basis of volume data representing a three-dimensional region that includes at least a part of the blood vessel region of a subject. The index image data generating circuitry 180 will be explained in detail later.

The combined data generating circuitry 190 (which may be referred to as "blood flow information data generating circuitry") is configured to generate combined data (which may be referred to as "blood flow information data") indicating a positional relationship between a blood flow information obtainment position and a blood vessel. The combined data generating circuitry 190 will be explained in detail later.

The transmitting and receiving circuitry 110 and the like installed in the apparatus main body 100 may be configured with hardware such as an integrated circuit or may be configured as a computer program structured with software by using modules.

Next, FIGS. 2A to 2C and FIGS. 3A to 3C are drawings illustrating the positional relationship between the blood vessel extending direction and the scanned position by the ultrasound wave. In the following section, for the sake of convenience in the explanation, the positional relationship between the blood vessel extending direction and the scanned position by the ultrasound wave will be explained by using a three-dimensional space defined by an X-axis, a Y-axis, and a Z-axis that are orthogonal to one another. More specifically, the central line of the blood vessel in a region of interest is defined as the X-axis. In that situation, the X-axis direction is the blood vessel extending direction and is the direction corresponding to the long-axis direction of the blood vessel. The Y-axis is a direction orthogonal to the blood vessel extending direction and the direction corresponding to the short-axis direction of the blood vessel.

In this situation, the "scanned position by the ultrasound wave" may refer to the entirety of a two-dimensional scanned plane or may refer to one ultrasound beam. In the following sections, it is assumed that a three-dimensional ultrasound beam is transmitted from the ultrasound probe 1, and a scanned plane that is positioned substantially at the center among a plurality of two-dimensional scanned planes will be referred to as a "representative scanned plane". Further, among a plurality of ultrasound beams transmitted to the inside of the representative scanned plane, such an ultrasound beam that is transmitted substantially from the center of the ultrasound probe 1 will be referred to as a "center beam".

Figure 2A:
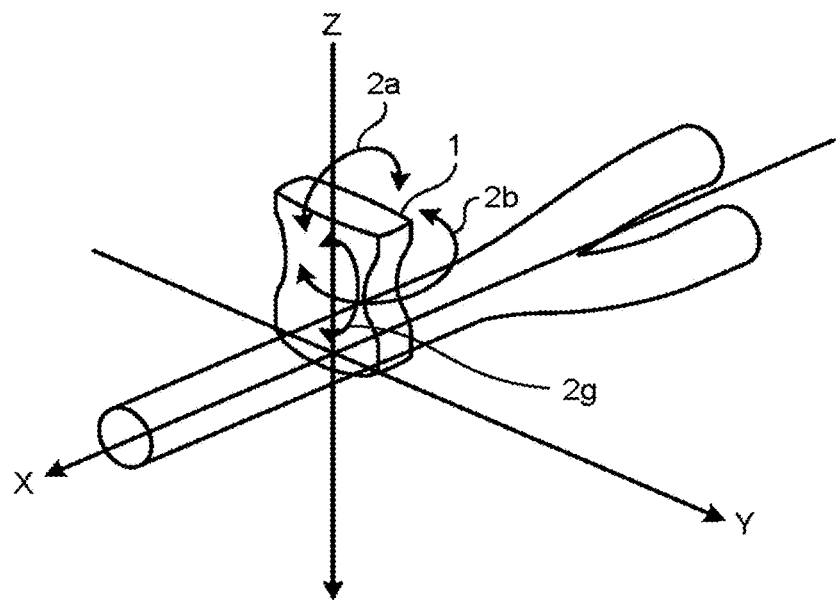
FIG. 2A is a drawing that illustrates a positional relationship between a blood vessel extending direction and a scanned position by an ultrasound wave.

In the example illustrated in FIG. 2A, the ultrasound probe 1 is positioned so as to scan the blood vessel to obtain a short-axis image. Generally speaking, in order to improve the precision level of diagnoses on stenoses in blood vessels, it is desirable to obtain accurate blood flow information. The ultrasound diagnosis apparatus renders an accurate short-axis image, when transmitting the center beam of an ultrasound wave to the inside of a cross-sectional plane that is orthogonal to the blood vessel extending direction and that corresponds to a short-axis cross-sectional plane of the blood vessel. By varying the transmission direction of the ultrasound beam while in that state so as to include the component in the blood vessel extending direction, the ultrasound diagnosis apparatus is able to obtain accurate blood flow information. In other words, when transmitting the center beam of the ultrasound wave to the inside of the cross-sectional plane that is orthogonal to the blood vessel extending direction and that corresponds to the short-axis direction of the blood vessel, the ultrasound probe 1 is considered to be positioned in a desirable position for obtaining the blood flow information, because it is possible to, for example, arrange the angle of the transmission direction of the ultrasound beam with respect to the blood vessel extending direction to be a known angle. In the description below, the cross-sectional plane that is orthogonal to the blood vessel extending direction and that corresponds to the short-axis direction of the blood vessel will be referred to as a "perpendicular plane during a short-axis image scan", or simply a "perpendicular plane".

Figure 2B:
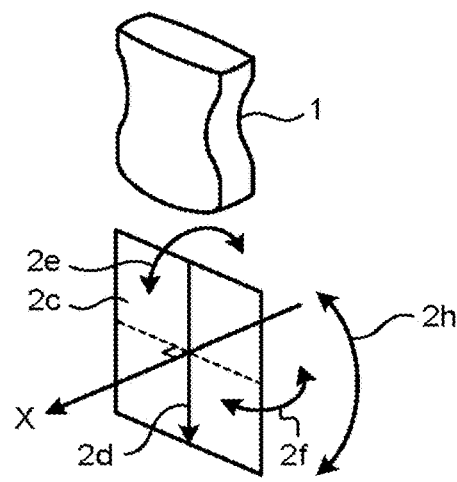
FIG. 2B is another drawing that illustrates the positional relationship between the blood vessel extending direction and the scanned position by the ultrasound wave.

FIG. 2B is a drawing for explaining an inclination of the scanned plane during the short-axis image scan. In the example illustrated in FIG. 2B, the scanned position by the ultrasound wave transmitted from the ultrasound probe 1 specifies a representative scanned plane 2c and a center beam 2d. For example, when scanning the blood vessel to obtain a short-axis image, it is desirable, as illustrated in FIG. 2B, to transmit an ultrasound wave in such a manner that the representative scanned plane 2c and the perpendicular plane during the short-axis image scan match each other.

However, in some situations, the ultrasound probe 1 operated by the operator may not be positioned so as to transmit an ultrasound wave in a desirable position. For example, if the ultrasound probe 1 illustrated in FIG. 2A is positioned so as to be inclined in a direction indicated by a bidirectional arrow 2a, because the representative scanned plane 2c is inclined in a direction indicated by a bidirectional arrow 2e illustrated in FIG. 2B, the representative scanned plane 2c and the perpendicular plane do not match each other and are in an intersecting positional relationship. As another example, if the ultrasound probe 1 illustrated in FIG. 2A is positioned so as to be inclined in a direction indicated by a bidirectional arrow 2b, because the representative scanned plane 2c is inclined in a direction indicated by a bidirectional arrow 2f illustrated in FIG. 2B, the representative scanned plane 2c and the perpendicular plane, again, do not match each other and are in an intersecting positional relationship.

Figure 2C:
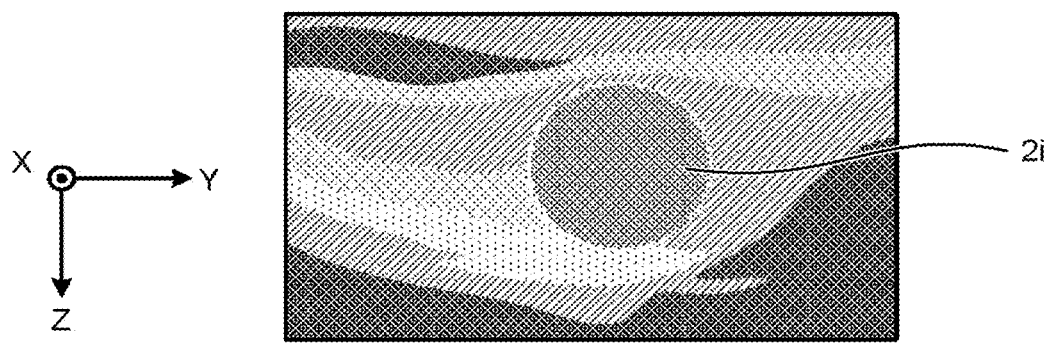
FIG. 2C is yet another drawing that illustrates the positional relationship between the blood vessel extending direction and the scanned position by the ultrasound wave.

For this reason, when performing a scan on a blood vessel so as to obtain a short-axis image, the operator such as a medical doctor checks to see whether the ultrasound probe 1 is positioned in such a manner that the representative scanned plane is orthogonal to the blood vessel extending direction, by viewing an ultrasound image displayed on the monitor 200 while moving the ultrasound probe 1. FIG. 2C is a drawing of an example of the blood vessel short-axis image. If the ultrasound probe 1 is transmitting an ultrasound wave onto a perpendicular plane, a blood vessel 2i during the short-axis image scan is rendered as a perfect circle, as illustrated in FIG. 2C. In contrast, if the ultrasound probe 1 is not transmitting an ultrasound wave onto a perpendicular plane, the blood vessel during the short-axis image scan is rendered as an oval. Accordingly, for example, the operator checks to see whether the blood vessel rendered in the ultrasound image is a perfect circle or not by viewing the ultrasound image.

It should be noted that, for example, when the ultrasound probe 1 illustrated in FIG. 2A is positioned so as to be inclined in a direction indicated by a bidirectional arrow 2g, the representative scanned plane 2c is inclined in a direction indicated by a bidirectional arrow 2h illustrated in FIG. 2B. As a result, the center beam 2d inside the representative scanned plane 2c no longer goes through the X-axis. Although it is considered that this positioning does not make a large impact on the obtainment of the blood flow information, there is a possibility that, in that situation, the blood vessel rendered in the short-axis image may be displayed in a position away from the center of the ultrasound image.

Figure 3A:
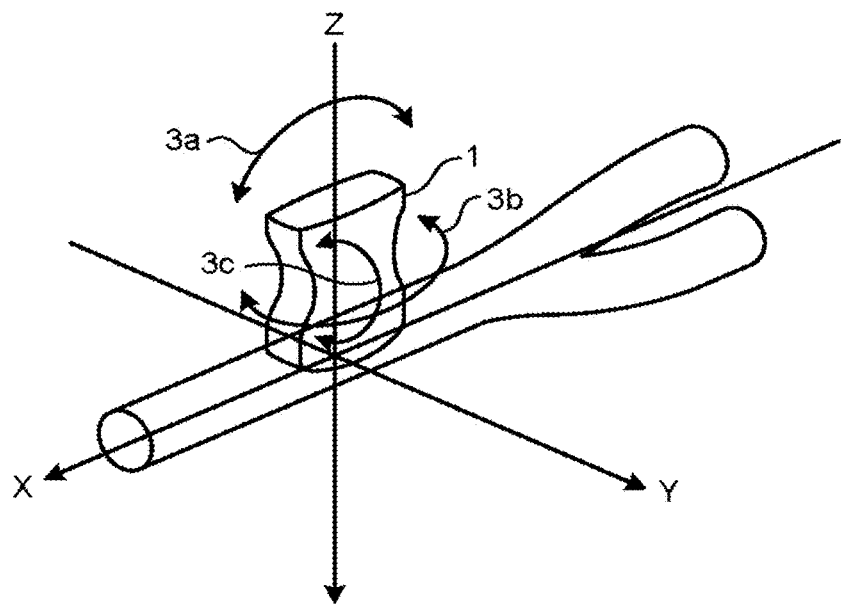
FIG. 3A is a drawing that illustrates a positional relationship between a blood vessel extending direction and a scanned position by an ultrasound wave.

In the next example illustrated in FIG. 3A, the ultrasound probe 1 is positioned so as to scan the blood vessel to obtain a long-axis image. The ultrasound diagnosis apparatus renders an accurate long-axis image, when transmitting the center beam of an ultrasound wave to the inside of a cross-sectional plane that is orthogonal to the blood vessel extending direction and that corresponds to a long-axis cross-sectional plane of the blood vessel. By varying the transmission direction of the ultrasound beam while in that state so as to include the component in the blood vessel extending direction, the ultrasound diagnosis apparatus is able to obtain accurate blood flow information. In other words, when transmitting the center beam of the ultrasound wave to the inside of the cross-sectional plane that is orthogonal to the blood vessel extending direction and that corresponds to the long-axis direction of the blood vessel, the ultrasound probe 1 is considered to be positioned in a desirable position for obtaining the blood flow information, because it is possible to, for example, arrange the angle of the transmission direction of the ultrasound beam with respect to the blood vessel extending direction to be a known angle. In the description below, the cross-sectional plane that is orthogonal to the blood vessel extending direction and that corresponds to the long-axis direction of the blood vessel will be referred to as a "perpendicular plane during a long-axis image scan", or simply a "perpendicular plane".

Figure 3B:
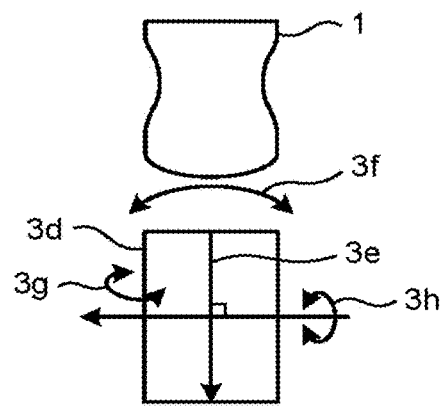
FIG. 3B is another drawing that illustrates the positional relationship between the blood vessel extending direction and the scanned position by the ultrasound wave.

FIG. 33 is a drawing for explaining an inclination of the scanned plane during the long-axis image scan. In the example illustrated in FIG. 3B, the scanned position by the ultrasound wave transmitted from the ultrasound probe 1 specifies a representative scanned plane 3d and a center beam 3e. For example, when scanning the blood vessel to obtain a long-axis image, it is desirable, as illustrated in FIG. 3B to transmit an ultrasound wave in such a manner that the representative scanned plane 3d and the perpendicular plane during the long-axis image scan match each other. Further, it is desirable to transmit the center beam 3e thereof in the direction orthogonal to the X-axis.

However, in some situations, the ultrasound probe 1 operated by the operator may not be positioned so as to transmit an ultrasound wave in a desirable position. For example, if the ultrasound probe 1 illustrated in FIG. 3A is positioned so as to be inclined in a direction indicated by a bidirectional arrow 3a, the representative scanned plane 3d is inclined in a direction indicated by a bidirectional arrow 3f illustrated in FIG. 3B. In that situation, the center beam 3e is not transmitted in the direction orthogonal to the X-axis.

As another example, if the ultrasound probe 1 illustrated in FIG. 3A is positioned so as to be inclined in a direction indicated by a bidirectional arrow 3b, because the representative scanned plane 3d is inclined in a direction indicated by a bidirectional arrow 3g illustrated in FIG. 3B, the representative scanned plane 3d and the perpendicular plane do not match each other and are in an intersecting positional relationship. In yet another example, if the ultrasound probe 1 illustrated in FIG. 3A is positioned so as to be inclined in a direction indicated by a bidirectional arrow 3c, because the representative scanned plane 3d is inclined in a direction indicated by a bidirectional arrow 3h illustrated in FIG. 3B, the representative scanned plane 3d and the perpendicular plane do not match each other and are in an intersecting positional relationship.

Figure 3C:
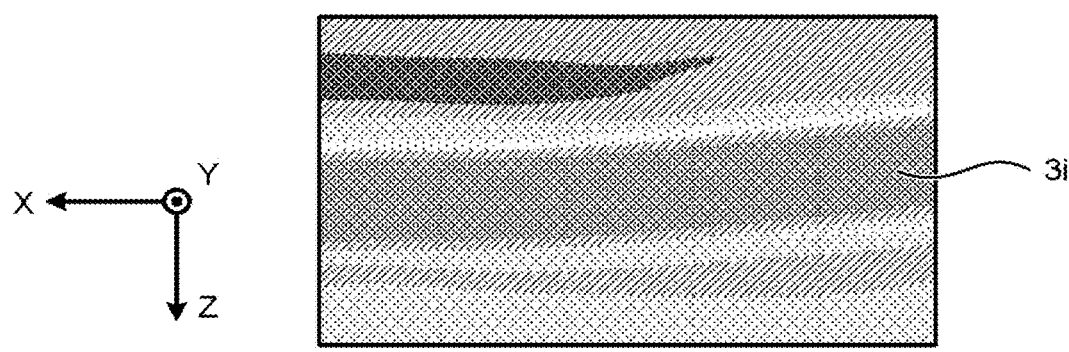
FIG. 3C is yet another drawing that illustrates the positional relationship between the blood vessel extending direction and the scanned position by the ultrasound wave.

A blood vessel during a long-axis image scan is rendered in a rectangular shape regardless of whether the ultrasound wave is transmitted to a desirable position or not. Accordingly, it is difficult for the operator to check to see whether the ultrasound wave is transmitted to a desirable position or not, by viewing an ultrasound image displayed on the monitor 200 while moving the ultrasound probe 1. For this reason, when scanning the blood vessel to obtain the long-axis image, the operator may, at first, position the ultrasound probe 1 in a position for a short-axis image scan and check to see whether the blood vessel in the short-axis image is rendered as a perfect circle or not by viewing the short-axis image, and subsequently, the operator may perform a long-axis image scan by turning the ultrasound probe 1 by 90 degrees. FIG. 3C is an example of a long-axis image. As illustrated in FIG. 3C, a blood vessel 3i during the long-axis image scan is rendered as a rectangle.

In this situation, as explained above, when performing the scan on the blood vessel to obtain the short-axis image, the operator checks to see whether the ultrasound probe 1 is positioned in a desirable position for starting the obtainment of obtainment information of the blood flow information, by viewing the ultrasound image displayed on the monitor 200 while moving the ultrasound probe 1. In other words, this judgment is based on subjectivity of the operator. Thus, even if the operator has determined that the ultrasound probe 1 is positioned in a desirable position for starting the obtainment of the blood flow information, there may be some situations where, in actuality, the ultrasound wave is not being transmitted to the inside of the perpendicular plane. In those situations, the ultrasound diagnosis apparatus is not able to obtain accurate blood flow information, even if the transmission direction of the ultrasound beam is varied in that state. Further, as explained above, when performing the scan on the blood vessel to obtain the long-axis image, the operator performs the long-axis image scan on the blood vessel by turning the ultrasound probe 1 by 90 degrees from the position of the short-axis image scan. In that situation also, because the operator positions the ultrasound probe 1 subjectively, there may be some situations where the ultrasound wave is not being transmitted to the inside of the perpendicular plane and in the direction orthogonal to the X-axis. In those situations also, the ultrasound diagnosis apparatus is not able to obtain accurate blood flow information, even if the transmission direction of the ultrasound beam is varied in that state. To cope with these situations, in the first embodiment, while an ultrasound image is being displayed, an index image is displayed, the index image including extending direction information that indicates the blood vessel extending direction and information that indicates the scanned position of the ultrasound wave transmitted from the ultrasound probe.

In the following sections, an operation of the index image data generating circuitry 180 will be explained in detail. The index image data generating circuitry 180 is configured to generate the extending direction information that indicates the blood vessel extending direction in a three-dimensional space on the basis of the volume data obtained by performing a three-dimensional ultrasound scan and to generate the index image data that includes the generated extending direction information and the information indicating the scanned position.

For example, the index image data generating circuitry 180 obtains the volume data from the image memory 150. Further, the index image data generating circuitry 180 extracts a blood vessel region from the volume data and calculates the blood vessel extending direction. Further, the index image data generating circuitry 180 generates index image data in which the information indicating the scanned position by the ultrasound wave transmitted from the ultrasound probe 1 and the blood vessel extending direction are superimposed on a schematic drawing of the blood vessel. In this situation, the information indicating the scanned position is expressed as either an arrow indicating the center beam or a straight line or a rectangle indicating the representative scanned plane. Alternatively, the operator is also able to judge the scanned position specifying the center beam or the representative scanned plane on the basis of the position of the ultrasound probe 1. For this reason, the information indicating the scanned position includes a schematic drawing of the ultrasound probe, as information indicating the position of the ultrasound probe 1. Further, because the information indicating the scanned position by the ultrasound wave is set by the transmitting and receiving circuitry 110 and is used by the image data generating circuitry 140, the index image data generating circuitry 180 obtains this information from either the transmitting and receiving circuitry 110 or the image data generating circuitry 140.

Next, the index image data generated by the index image data generating circuitry 180 will be explained. In the following sections, examples in which blood flow information during a short-axis image scan is obtained will be explained with reference to FIGS. 4A to 4C and FIGS. 5A to 5C. Further, an example in which blood flow information during a long-axis image scan is obtained will be explained with reference to FIGS. 6A to 6C and FIGS. 7A to 7C. To refer to directions in FIGS. 4A to 7C, the three-dimensional space defined in FIGS. 2A to 2C and FIGS. 3A to 3C will be used.

Figure 4A:
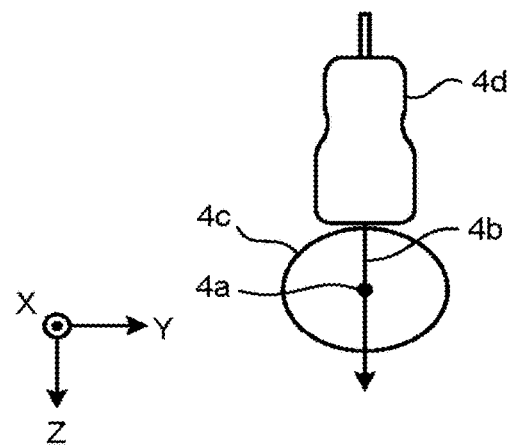
FIG. 4A is a drawing of an example of index image data generated by index image data generating circuitry.
Figure 4B:
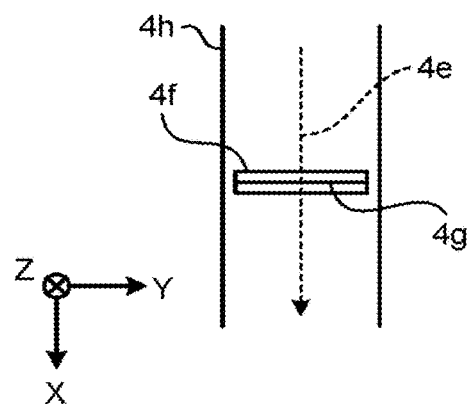
FIG. 4B is a drawing of another example of the index image data generated by the index image data generating circuitry.
Figure 4C:
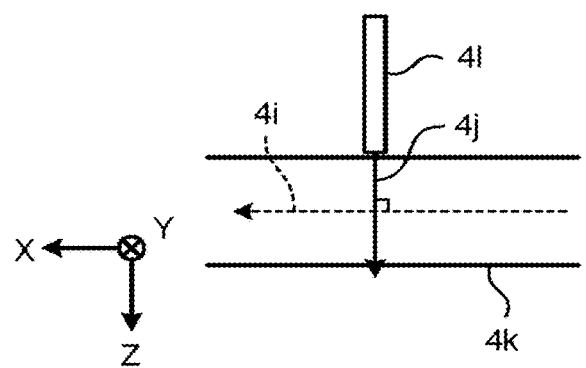
FIG. 4C is a drawing of yet another example of the index image data generated by the index image data generating circuitry.

First, an example will be explained in which, when blood flow information is obtained while a blood vessel is scanned so as to obtain a short-axis image, the ultrasound probe 1 is positioned so as to transmit an ultrasound wave to the inside of a plane that is orthogonal to the blood vessel extending direction. This situation corresponds to when the ultrasound probe 1 is positioned in a desirable position for starting the obtainment of the blood flow information. FIGS. 4A to 4C are drawings of examples of index image data generated by the index image data generating circuitry 180.

FIG. 4A is a drawing of an example of index image data generated by the index image data generating circuitry 180 corresponding to when the blood vessel illustrated in FIG. 2A is viewed from the X-axis direction. In the example illustrated in FIG. 4A, the index image data generating circuitry 180 generates index image data in which an extending direction 4a, a center beam 4b, and a schematic drawing of an ultrasound probe 4d are superimposed on a schematic drawing of a blood vessel 4c. In this situation, the extending direction 4a illustrated in FIG. 4A is displayed as a point. If the ultrasound probe 1 is positioned in a desirable position, as illustrated in FIG. 4A, the center beam 4b goes through the X-axis, whereas the schematic drawing of the ultrasound probe 4d is positioned perpendicular to the Y-axis, in the index image data generated by the index image data generating circuitry 180.

FIG. 4B is a drawing of an example of index image data generated by the index image data generating circuitry 180 corresponding to when the blood vessel illustrated in FIG. 2A is viewed from the Z-axis direction. In the example illustrated in FIG. 4B, the index image data generating circuitry 180 generates index image data in which an extending direction 4e, a schematic drawing of an ultrasound probe 4f, and a representative scanned plane 4g are superimposed on a schematic drawing of a blood vessel 4h. In this situation, the representative scanned plane 4g illustrated in FIG. 4B is displayed as a straight line. If the ultrasound probe 1 is positioned in a desirable position, as illustrated in FIG. 4B, the extending direction 4e and the schematic drawing of the ultrasound probe 4f are substantially orthogonal to each other, whereas the extending direction 4e and the representative scanned plane 4g are substantially orthogonal to each other, in the index image data generated by the index image data generating circuitry 180.

FIG. 4C is a drawing of an example of index image data generated by the index image data generating circuitry 180 corresponding to when the blood vessel illustrated in FIG. 2A is viewed from the Y-axis direction. In the example illustrated in FIG. 4C, the index image data generating circuitry 180 generates index image data in which an extending direction 4i, a center beam 4j, and a schematic drawing of an ultrasound probe 4l are superimposed on a schematic drawing of a blood vessel 4k. In this situation, although FIG. 4C illustrates the center beam 4j, the representative scanned plane is also displayed to be the same as the center beam 4j. If the ultrasound probe 1 is positioned in a desirable position, as illustrated in FIG. 4C, the extending direction 4i and the center beam (the representative scanned plane) 4j are substantially orthogonal to each other, whereas the schematic drawing of the ultrasound probe is positioned perpendicular to the X-axis, in the index image data generated by the index image data generating circuitry 180.

Next, examples will be explained in which, when blood flow information is obtained while a blood vessel is scanned so as to obtain a short-axis image, the ultrasound probe 1 is not positioned so as to transmit an ultrasound wave to the inside of a plane that is orthogonal to the blood vessel extending direction. This situation corresponds to when the ultrasound probe 1 is not positioned in a desirable position for starting the obtainment of the blood flow information.

Figure 5A:
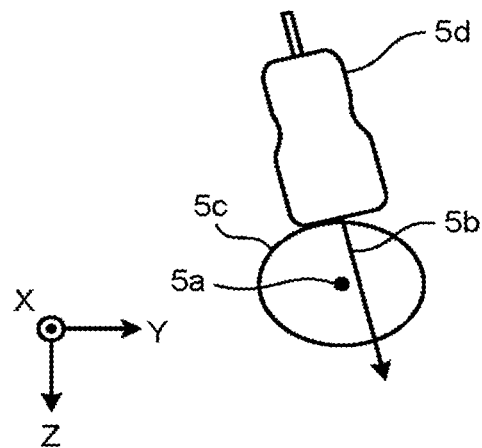
FIG. 5A is a drawing of yet another example of the index image data generated by the index image data generating circuitry.
Figure 5B:
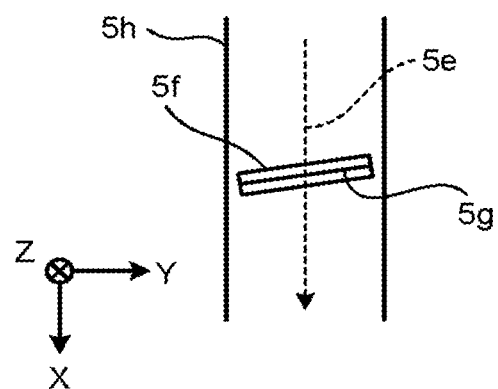
FIG. 5B is a drawing of yet another example of the index image data generated by the index image data generating circuitry.
Figure 5C:
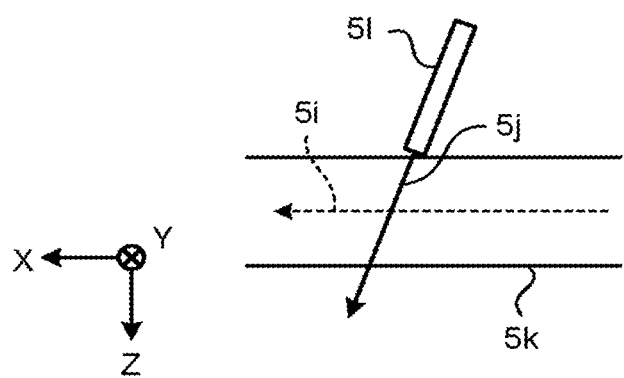
FIG. 5C is a drawing of yet another example of the index image data generated by the index image data generating circuitry.

FIGS. 5A to 5C are drawings of examples of index image data generated by the index image data generating circuitry 180.

FIG. 5A is a drawing of an example of index image data corresponding to when the ultrasound probe 1 illustrated in FIG. 2A being inclined in the 2g direction is viewed from the X-axis direction. In the example illustrated in FIG. 5A, the index image data generating circuitry 180 generates index image data in which an extending direction 5a, a center beam 5b, and a schematic drawing of an ultrasound probe 5d are superimposed on a schematic drawing of a blood vessel 5c. In this situation, the extending direction 5a illustrated in FIG. 5A is displayed as a point. If the ultrasound probe 1 is not positioned in a desirable position, as illustrated in FIG. 5A, the center beam 5b does not go through the X-axis, whereas the schematic drawing of the ultrasound probe 5d is not positioned perpendicular to the Y-axis, in the index image data generated by the index image data generating circuitry 180. As a result, when the center beam 5b does not go through the X-axis or when the schematic drawing of the ultrasound probe 5d is not positioned perpendicular to the Y-axis in the index image data corresponding to the view from the X-axis direction, the operator is able to determine that the blood vessel rendered in the short-axis image is displayed in a position away from the center of the ultrasound images.

FIG. 5B is a drawing of an example of index image data corresponding to when the ultrasound probe 1 illustrated in FIG. 2A being inclined in the 2b direction is viewed from the Z-axis direction. In the example illustrated in FIG. 5B, the index image data generating circuitry 180 generates index image data in which an extending direction 5e, a schematic drawing of an ultrasound probe 5f, and a representative scanned plane 5g are superimposed on a schematic drawing of a blood vessel 5h. In this situation, the representative scanned plane 5g illustrated in FIG. 5B is displayed as a straight line. If the ultrasound probe 1 is not positioned in a desirable position, as illustrated in FIG. 5B, the extending direction 5e and the schematic drawing of the ultrasound probe 5f are not orthogonal to each other, whereas the extending direction 5e and the representative scanned plane 5g are not substantially orthogonal to each other, in the index image data generated by the index image data generating circuitry 180. As a result, when the extending direction and the schematic drawing of the ultrasound probe are not substantially orthogonal to each other or when the extending direction and the representative scanned plane are not substantially orthogonal to each other in the index image data corresponding to the view from the Z-axis direction, the operator is able to determine that the ultrasound probe 1 is not positioned in a desirable position.

FIG. 5C is a drawing of an example of index image data corresponding to when the ultrasound probe 1 illustrated in FIG. 2A being inclined in the 2a direction is viewed from the Y-axis direction. In the example illustrated in FIG. 5C, the index image data generating circuitry 180 generates index image data in which an extending direction 5i, a center beam 5j, and a schematic drawing of an ultrasound probe 5l are superimposed on a schematic drawing of a blood vessel 5k. In this situation, although FIG. 5C illustrates the center beam 5j, the representative scanned plane is also displayed to be the same as the center beam 5j. If the ultrasound probe 1 is not positioned in a desirable position, as illustrated in FIG. 5C, the extending direction 5i and the center beam (the representative scanned plane) 5j are not orthogonal to each other, whereas the schematic drawing of the ultrasound probe is not positioned perpendicular to the X-axis, in the index image data generated by the index image data generating circuitry 180. As a result, when the extending direction and the center beam (or the representative scanned plane) are not substantially orthogonal to each other or when the schematic drawing of the ultrasound probe is not positioned perpendicular to the X-axis in the index image data corresponding to the view from the Y-axis direction, the operator is able to determine that the ultrasound probe 1 is not positioned in a desirable position.

Figure 6A:
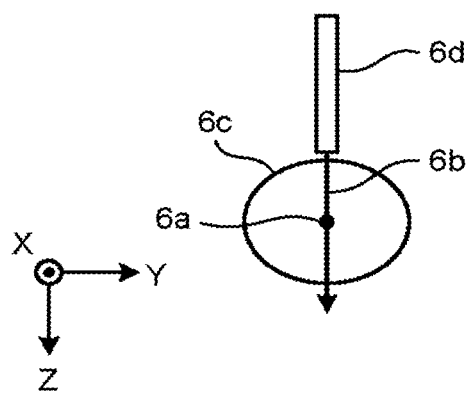
FIG. 6A is a drawing of yet another example of the index image data generated by the index image data generating circuitry.
Figure 6B:
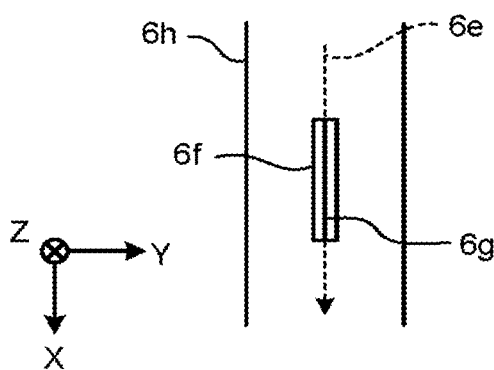
FIG. 6B is a drawing of yet another example of the index image data generated by the index image data generating circuitry.
Figure 6C:
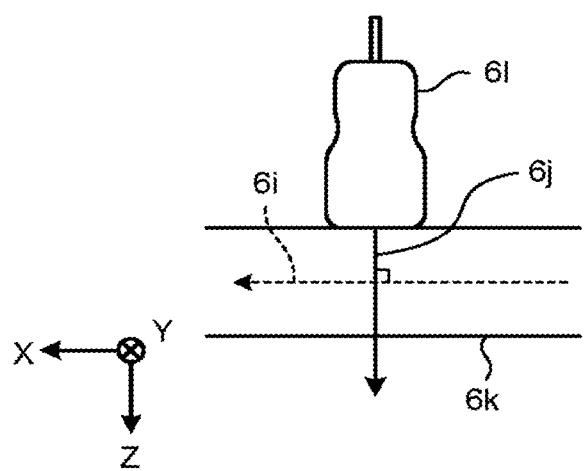
FIG. 6C is a drawing of yet another example of the index image data generated by the index image data generating circuitry.

Next, examples will be explained in which, when blood flow information is obtained while a blood vessel is scanned so as to obtain a long-axis image, the ultrasound probe 1 is positioned so as to transmit an ultrasound wave to the inside of a plane that is orthogonal to the short axis of the blood vessel and in a direction orthogonal to the blood vessel extending direction. This situation corresponds to when the ultrasound probe 1 is positioned in a desirable position for starting the obtainment of the blood flow information. FIGS. 6A to 6C are drawings of examples of index image data generated by the index image data generating circuitry 180.

FIG. 6A is a drawing of an example of index image data generated by the index image data generating circuitry 180 corresponding to when the blood vessel illustrated in FIG. 3A is viewed from the X-axis direction. In the example illustrated in FIG. 6A, the index image data generating circuitry 180 generates index image data in which an extending direction 6a, a center beam 6b, and a schematic drawing of an ultrasound probe 6d are superimposed on a schematic drawing of a blood vessel 6c. In this situation, the extending direction 6a illustrated in FIG. 6A is displayed as a point. Further, although FIG. 6A illustrates the center beam 6b, the representative scanned plane is also displayed to be the same as the center beam 6b. If the ultrasound probe 1 is positioned in a desirable position, as illustrated in FIG. 6A, the center beam (the representative scanned plane) 6b goes through the X-axis, whereas the schematic drawing of the ultrasound probe 6d is positioned perpendicular to the Y-axis, in the index image data generated by the index image data generating circuitry 180.

FIG. 6B is a drawing of an example of index image data generated by the index image data generating circuitry 180 corresponding to when the blood vessel illustrated in FIG. 3A is viewed from the Z-axis direction. In the example illustrated in FIG. 6B, the index image data generating circuitry 180 generates index image data in which an extending direction 6e, a schematic drawing of an ultrasound probe 6f, and a representative scanned plane 6g are superimposed on a schematic drawing of a blood vessel 6h. In this situation, the representative scanned plane 6g illustrated in FIG. 6B is displayed as a straight line. If the ultrasound probe 1 is positioned in a desirable position, as illustrated in FIG. 6B, the extending direction 6e and the schematic drawing of the ultrasound probe 6f substantially match each other, whereas the extending direction 6e and the representative scanned plane 6g substantially match each other, in the index image data generated by the index image data generating circuitry 180.

FIG. 6C is a drawing of an example of index image data generated by the index image data generating circuitry 180 corresponding to when the blood vessel illustrated in FIG. 3A is viewed from the Y-axis direction. In the example illustrated in FIG. 6C, the index image data generating circuitry 180 generates index image data in which an extending direction 6i, a center beam 6j, and a schematic drawing of an ultrasound probe 6l are superimposed on a schematic drawing of a blood vessel 6k. If the ultrasound probe 1 is positioned in a desirable position, as illustrated in FIG. 6C, the extending direction 6i and the center beam 6j are substantially orthogonal to each other, whereas the schematic drawing of the ultrasound probe is positioned perpendicular to the X-axis, in the index image data generated by the index image data generating circuitry 180.

Figure 7A:
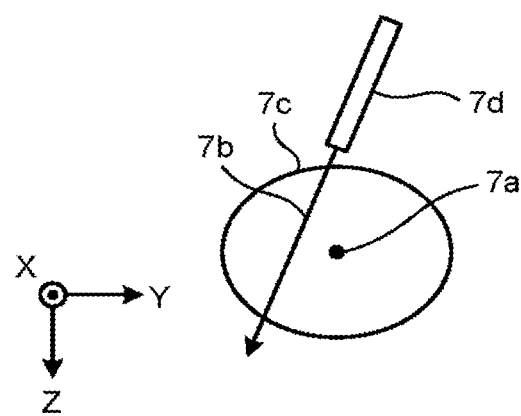
FIG. 7A is a drawing of yet another example of the index image data generated by the index image data generating circuitry.
Figure 7B:
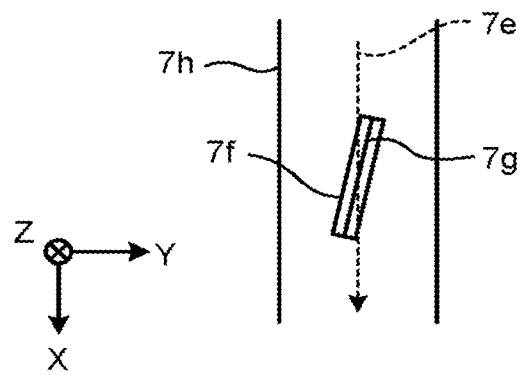
FIG. 7B is a drawing of yet another example of the index image data generated by the index image data generating circuitry.
Figure 7C:
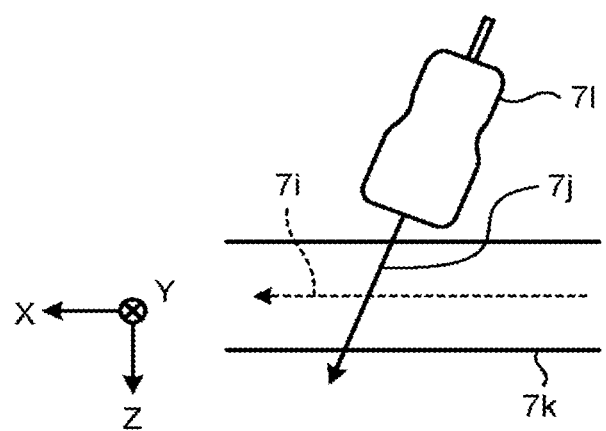
FIG. 7C is a drawing of yet another example of the index image data generated by the index image data generating circuitry.

Next, examples will be explained in which, when blood flow information is obtained with a long-axis image of a blood vessel, the ultrasound probe 1 is not positioned so as to transmit an ultrasound wave to the inside of a plane that is orthogonal to the short axis of the blood vessel and in the direction orthogonal to the blood vessel extending direction. This situation corresponds to when the ultrasound probe 1 is not positioned in a desirable position for starting the obtainment of the blood flow information. FIGS. 7A to 7C are drawings of examples of index image data generated by the index image data generating circuitry 180.

FIG. 7A is a drawing of an example of index image data corresponding to when the ultrasound probe 1 illustrated in FIG. 3A being inclined in the 3c direction is viewed from the X-axis direction. In the example illustrated in FIG. 7A, the index image data generating circuitry 180 generates index image data in which an extending direction 7a, a center beam 7b, and a schematic drawing of an ultrasound probe 7d are superimposed on a schematic drawing of a blood vessel 7c. In this situation, the extending direction 7a illustrated in FIG. 7A is displayed as a point. Although FIG. 7A illustrates the center beam 7b, the representative scanned plane is also displayed to be the same as the center beam 7b. If the ultrasound probe 1 is not positioned in a desirable position, as illustrated in FIG. 7A, the center beam (the representative scanned plane) 7b does not go through the X-axis, whereas the schematic drawing of the ultrasound probe 7d is not positioned perpendicular to the Y-axis, in the index image data generated by the index image data generating circuitry 180. As a result, when the center beam or the representative scanned plane does not go through the X-axis or when the schematic drawing of the ultrasound probe is not positioned perpendicular to the Y-axis in the index image data corresponding to the view from the X-axis direction, the operator is able to determine that the ultrasound probe 1 is not positioned in a desirable position.

FIG. 7B is a drawing of an example of index image data corresponding to when the ultrasound probe 1 illustrated in FIG. 3A being inclined in the 3b direction is viewed from the Z-axis direction. In the example illustrated in FIG. 7B, the index image data generating circuitry 180 generates index image data in which an extending direction 7e, a schematic drawing of an ultrasound probe 7f, and a representative scanned plane 7g are superimposed on a schematic drawing of a blood vessel 7h. In this situation, the representative scanned plane 7g illustrated in FIG. 7B is displayed as a straight line. If the ultrasound probe 1 is not positioned in a desirable position, as illustrated in FIG. 7B, the extending direction 7e and the schematic drawing of the ultrasound probe 7f do not match each other, whereas the extending direction 7e and the representative scanned plane 7g do not match each other, in the index image data generated by the index image data generating circuitry 180. As a result, when the extending direction and the schematic drawing of the ultrasound probe do not match each other or when the extending direction and the representative scanned plane do not match each other in the index image data corresponding to the view from the Z-axis direction, the operator is able to determine that the ultrasound probe 1 is not positioned in a desirable position.

FIG. 7C is a drawing of an example of index image data corresponding to when the ultrasound probe 1 illustrated in FIG. 3A being inclined in the 3a direction is viewed from the Y-axis direction. In the example illustrated in FIG. 7C, the index image data generating circuitry 180 generates index image data in which an extending direction 7i, a center beam 7j, and a schematic drawing of an ultrasound probe 7l are superimposed on a schematic drawing of a blood vessel 7k. If the ultrasound probe 1 is not positioned in a desirable position, as illustrated in FIG. 7C, the extending direction 7i and the center beam 7j are not orthogonal to each other, whereas the schematic drawing of the ultrasound probe 7l is not positioned perpendicular to the X-axis, in the index image data generated by the index image data generating circuitry 180. As a result, when the extending direction and the center beam are not substantially orthogonal to each other or when the schematic drawing of the ultrasound probe is not positioned perpendicular to the X-axis in the index image data corresponding to the view from the Y-axis direction, the operator is able to determine that the ultrasound probe 1 is not positioned in a desirable position.

Figure 8:
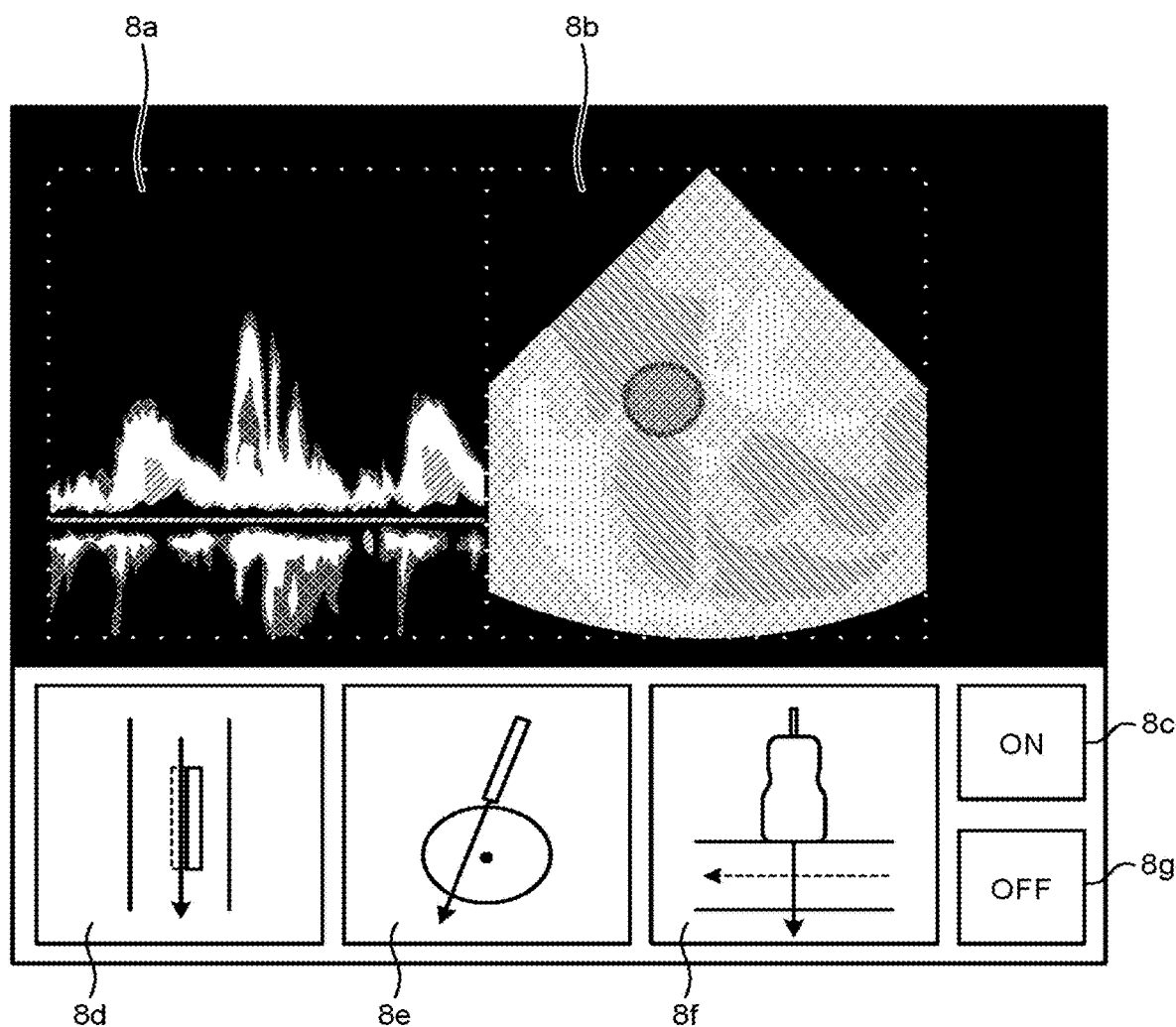
FIG. 8 is a drawing of an example of index image data displayed on a monitor by controlling circuitry.

The index image data generated by the index image data generating circuitry 180 in this manner is displayed on the monitor 200 by the controlling circuitry 170. In this situation, the controlling circuitry 170 causes the index image data to be displayed in a part of the area of the monitor 200. FIG. 8 is a drawing of an example of the index image data displayed on the monitor 200 by the controlling circuitry 170. The example in FIG. 8 illustrates a situation where the pulse Doppler mode is selected. As illustrated in FIG. 8, the controlling circuitry 170 causes a pulse Doppler image 8a to be displayed on the upper left side of the area of the monitor 200 and causes a B-mode image 8b to be displayed on the upper right side of the area of the monitor 200. Further, the controlling circuitry 170 causes an ON button 8c that starts the display of the index image data and an OFF button 8g that ends the display of the index image data to be displayed on the lower right side of the area of the monitor 200. While the pulse Doppler mode is selected, the pulse Doppler image 8a, the B-mode image 8b, the ON button 8c, and the OFF button 8g illustrated in FIG. 8 are displayed on the monitor 200. If the color Doppler mode is selected, for example, a color image (a color Doppler image) is displayed while being superimposed on a B-mode image.

Further, when having received an operation to press the ON button 8c, for example, the controlling circuitry 170 causes pieces of index image data 8d to 8f to be displayed. In the example illustrated in FIG. 8, the controlling circuitry 170 causes the index image data 8d corresponding to the view from the Z-axis direction to be displayed on the lower left side of the area of the monitor 200, causes the index image data 8e corresponding to the view from the X-axis direction to be displayed on the lower middle side of the area of the monitor 200, and causes the index image data 0f corresponding to the view from the Y-axis direction to be displayed on the lower right side of the area of the monitor 200. It should be noted that the positions in which the pieces of index image data 8d to 8f can be displayed are not limited to those illustrated in the drawing.

In contrast, when having received an operation to press the OFF button 8g, for example, the controlling circuitry 170 stops the display of the pieces of index image data 8d to 8f. In that situation, while the pulse Doppler mode is selected, the pulse Doppler image 8a, the B-mode image 8b, the ON button 8c, and the OFF button 8g are displayed on the monitor 200. As explained above, the display of the index image data is controlled with timing independent of the timing for the display of the Doppler image data or the B-mode image data.

Next, an operation of the combined data generating circuitry 190 will be explained in detail. The combined data generating circuitry 190 (which may be referred to as "blood flow data generating circuitry") is configured to generate combined data (which may be referred to as "blood flow data") that indicates a positional relationship between a blood flow information obtainment position and the blood vessel.

For example, when having received an instruction from the operator to generate combined data after a scan is finished, the combined data generating circuitry 190 generates the combined data by expressing that partitions that each have a substantially circular shape or a substantially oval shape are positioned in a schematic drawing of the blood vessel that is substantially in the shape of a circular cylinder. More specifically, the combined data generating circuitry 190 reads information in which the scanned positions in the blood vessel and pieces of blood flow information at the scanned positions are kept in correspondence with one another, from the image memory 150. After that, the combined data generating circuitry 190 generates the combined data in which positional relationships of the scanned positions in the blood vessel are combined with the schematic drawing of the blood vessel, on the basis of the read information. Further, the combined data generating circuitry 190 brings the pieces of blood flow information obtained at the scanned positions into correspondence with the scanned positions. Alternatively, if the scanned positions include angle information about scanning lines with respect to the blood vessel extending direction corresponding to when the pieces of blood flow information were obtained, the partitions may be inclined on the basis of the angle information.

Figure 9:
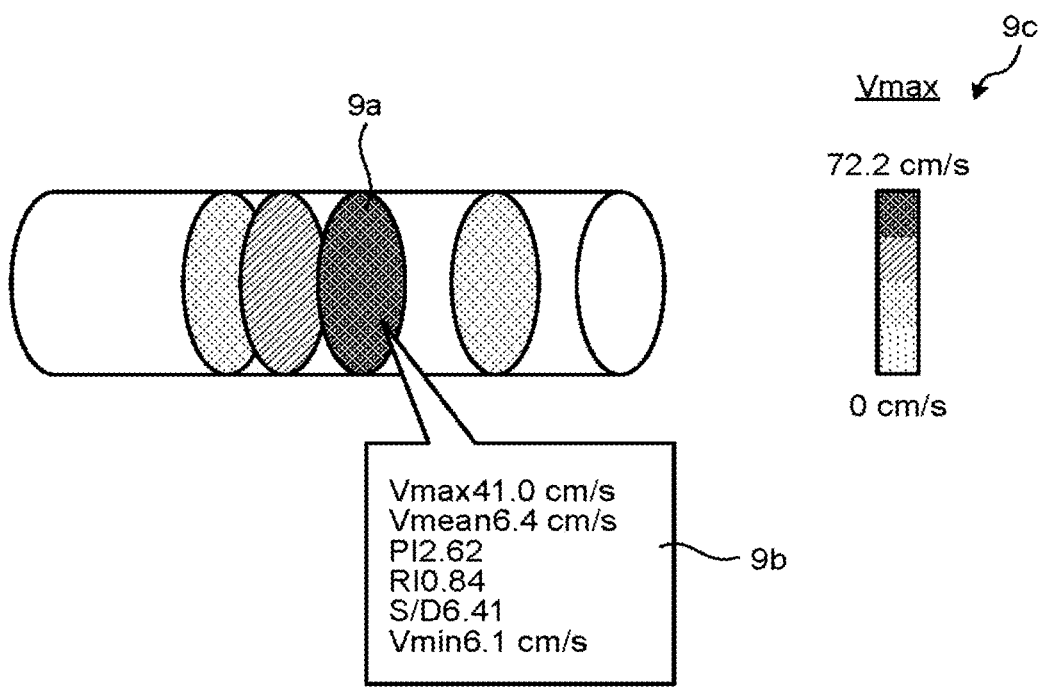
FIG. 9 is a drawing of an example of combined data displayed on the monitor via the controlling circuitry.

The combined data generated by the combined data generating circuitry 190 in this manner is displayed on the monitor 200 via the controlling circuitry 170. FIG. 9 is a drawing of an example of the combined data displayed on the monitor 200 via the controlling circuitry 170. As illustrated in FIG. 9, when having received an instruction from the operator to display the combined data, for example, the combined data generating circuitry 190 causes the monitor 200 to display the combined data via the controlling circuitry 170. The example in FIG. 9 illustrates combined data in which positional relationships between four scanned positions and the blood vessel are schematically expressed. In FIG. 9, the circular cylinder corresponds to the blood vessel, whereas the circles rendered in colors in the circular cylinder correspond to the scanned positions.

Further, when having received a selection of a measuring position, the combined data generating circuitry 190 causes the monitor 200 to display the piece of blood flow information that is kept in correspondence with the selected measuring position. For example, when a cursor is placed on one of the scanned positions, the combined data generating circuitry 190 displays the piece of blood flow information corresponding to the scanned position on which the cursor is placed. In the example illustrated in FIG. 9, when the cursor is placed on a scanned position 9a, the combined data generating circuitry 190 displays a piece of blood flow information 9b corresponding to the scanned position 9a. Examples of different types of blood flow information displayed in the present example include "Vmax", "Vmin", "Vmean", "Pulsatility Index (PI)", "Resistance Index (RI)", and "S/D". In this situation, "Vmax" denotes a systolic maximum blood flow rate; "Vmin" denotes an end-diastolic blood flow rate; "Vmean" denotes an average blood flow rate; "PI" denotes a pulsatility coefficient; "RI" denotes a resistance coefficient; and "S/D" denotes a ratio of the systolic maximum flow rate to the end-diastolic flow rate. In the present example, "RI" can be calculated from "(Vmax−Vmin)/Vmax". "PI" can be calculated from "(Vmax−Vmin)/Vmean".

Further, the combined data generating circuitry 190 generates the combined data in which each of the partitions that each have the substantially circular shape or the substantially oval shape and that correspond to the measuring positions is colored in accordance with the value of the blood flow rate at the corresponding measuring position. For example, when one of the types of blood flow information has been selected, the combined data generating circuitry 190 changes the display modes of the combined data displayed on the monitor 200 in accordance with the values of the blood flow rates corresponding to the selected type. In the example illustrated in FIG. 9, when "Vmax" has been selected as the type, the combined data generating circuitry 190 displays a color bar 9c indicating the correspondence relationship between ranges of the values of "Vmax" and colors. Further, the combined data generating circuitry 190 changes the display color corresponding to each of the scanned positions in accordance with the value of Vmax at the scanned position. Further, the positions of the scanned positions in the combined data may be kept in correspondence with the positions thereof in the actual blood vessel.

Figure 10:
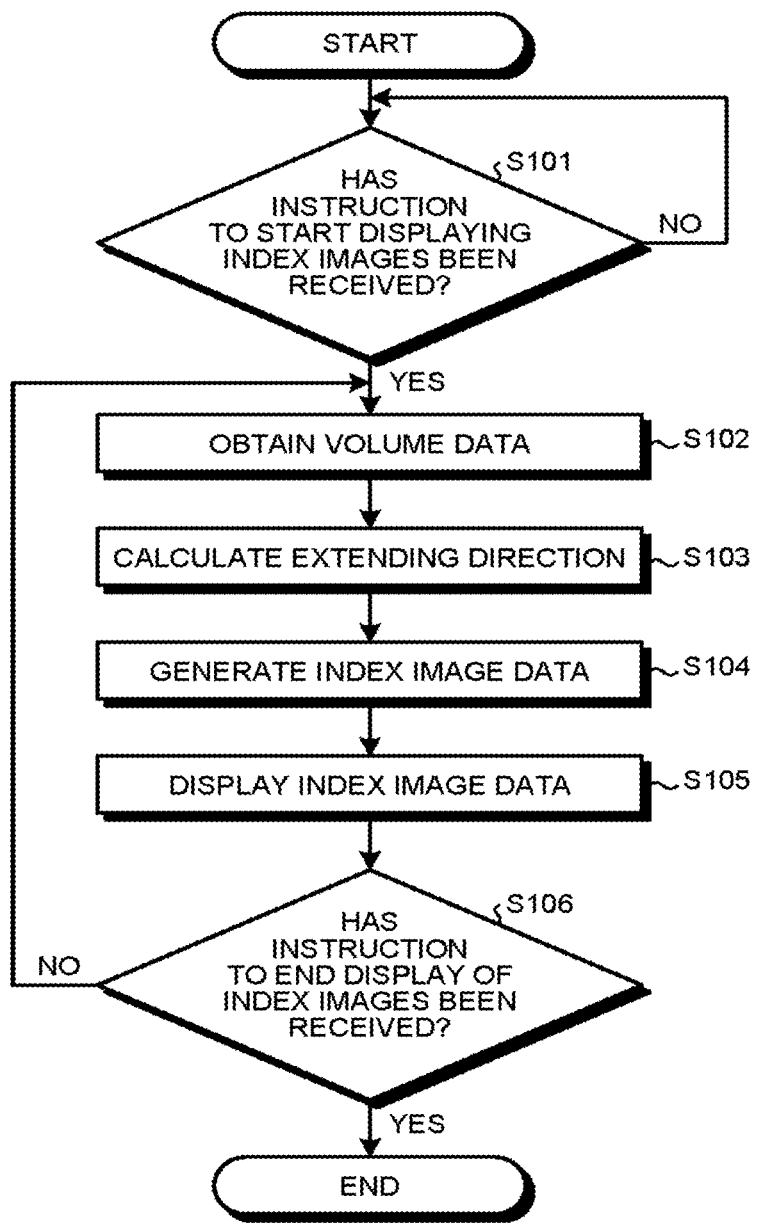
FIG. 10 is a flowchart of a processing procedure performed by the index image data generating circuitry according to the first embodiment.

Next, a processing procedure performed by the index image data generating circuitry 180 will be explained with reference to FIG. 10. FIG. 10 is a flowchart of the processing procedure performed by the index image data generating circuitry 180 according to the first embodiment. As illustrated in FIG. 10, the index image data generating circuitry 180 judges whether or not an instruction to start displaying one or more index images has been received (step S101). In this situation, when having determined that an instruction to start displaying index images is received (step S101: Yes), the index image data generating circuitry 180 obtains the volume data from the image memory 150 (step S102). On the contrary, if the index image data generating circuitry 180 does not determine that an instruction to start displaying index images is received (step S101: No), the index image data generating circuitry 180 repeatedly performs the judging process at step S101.

On the basis of the obtained volume data, the index image data generating circuitry 180 calculates the extending direction (step S103). Further, the index image data generating circuitry 180 generates index image data that includes the calculated extending direction and information indicating scanned positions by the ultrasound wave (step S104). After that, the index image data generating circuitry 180 causes the monitor 200 to display the generated index image data via the controlling circuitry 170 (step S105).

The index image data generating circuitry 180 judges whether or not an instruction to end the display of the index images has been received (step S106). When having determined that an instruction to end the display of the index images is received (Step S106: Yes), the index image data generating circuitry 180 ends the index image generating process. On the contrary, if the index image data generating circuitry 180 does not determine that an instruction to end the display of the index images is received (step S106: No), the process proceeds to step S102, where the volume data is obtained (step S102). With this arrangement, the index image data generating circuitry 180 continues to generate index image data in a real-time manner until an instruction to end the display is received. Further, as a result, index image data corresponding to the current inclination state of the ultrasound probe 1 continues to be displayed on the monitor 200 in a real-time manner.

Figure 11:
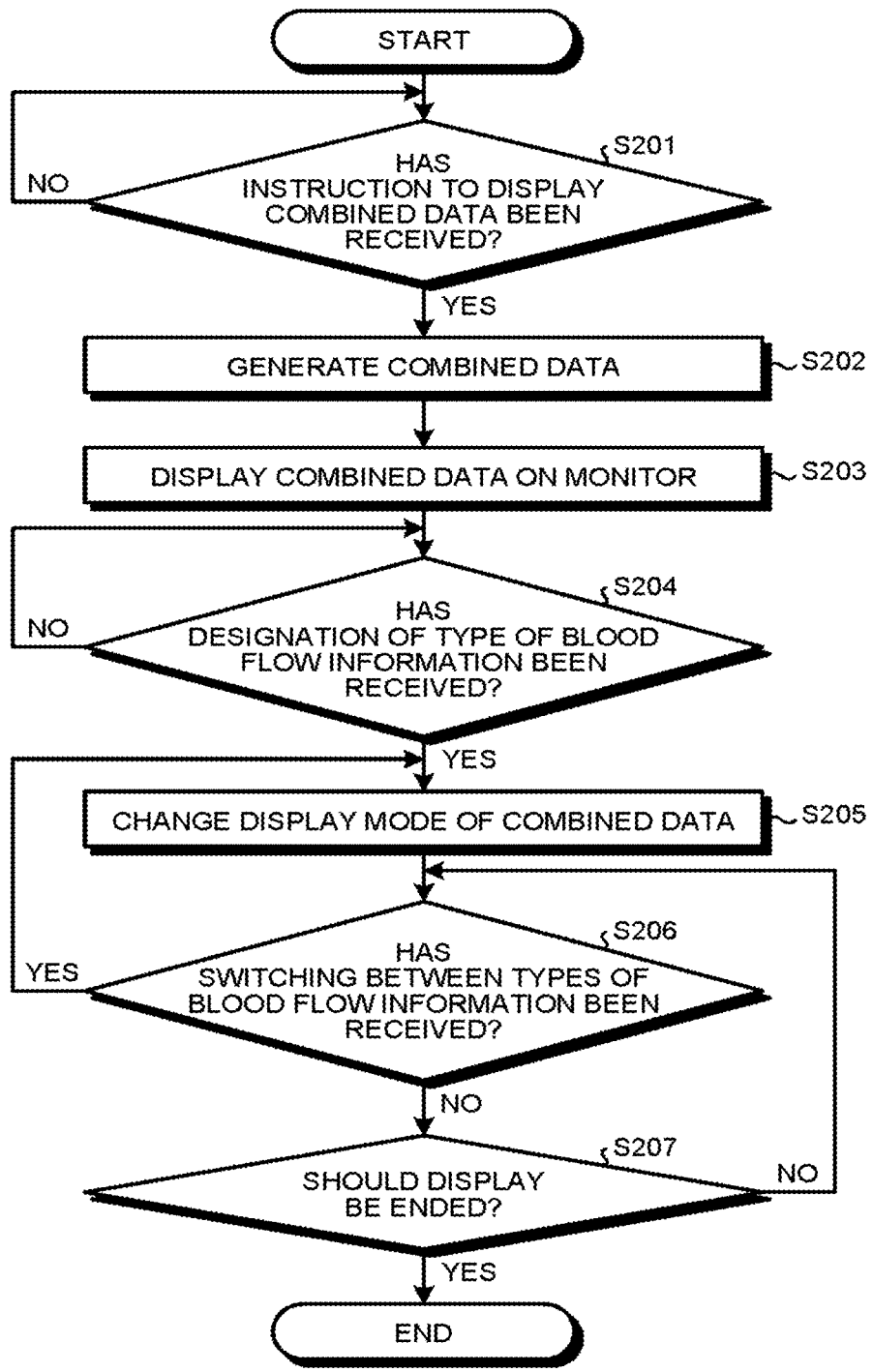
FIG. 11 is a flowchart of a processing procedure performed by combined data generating circuitry according to the first embodiment.

Next, a processing procedure performed by the combined data generating circuitry 190 will be explained with reference to FIG. 11. FIG. 11 is a flowchart of the processing procedure performed by the combined data generating circuitry 190 according to the first embodiment. As illustrated in FIG. 11, the combined data generating circuitry 190 judges whether or not an instruction to display combined data has been received (step S201). In this situation, when having determined that an instruction to display combined data is received (step S201: Yes), the combined data generating circuitry 190 reads the information in which the scanned positions in the blood vessel are kept in correspondence with the pieces of blood flow information at the scanned positions, from the image memory 150 and generates the combined data (step S202). On the contrary, if the combined data generating circuitry 190 does not determine that an instruction to display combined data is received (step S201: No), the combined data generating circuitry 190 repeatedly perform the judging process at step S201.

Subsequently, the combined data generating circuitry 190 causes the monitor 200 to display the generated combined data via the controlling circuitry 170 (step S203). After that, the combined data generating circuitry 190 judges whether or not a designation of a type of blood flow information has been received (step S204). In this situation, when having determined that a designation of a type of blood flow information is received (step S204: Yes), the combined data generating circuitry 190 changes the display mode of the combined data (step S205). On the contrary, if the combined data generating circuitry 190 does not determine that a designation of a type of blood flow information is received (step S204: No), the combined data generating circuitry 190 repeatedly performs the judging process at step S204.

After that, the combined data generating circuitry 190 judges whether or not switching between types of blood flow information has been received (step S206). In this situation, if the combined data generating circuitry 190 has determined that switching between types of blood flow information is received (step S206: Yes), the process proceeds to step S205 where the display mode of the combined data is changed (step S205).

On the contrary, if the combined data generating circuitry 190 does not determine that switching between types of blood flow information is received (step S206: No), the combined data generating circuitry 190 judges whether or not an instruction to end the display has been received (step S207). In this situation, if the combined data generating circuitry 190 does not determine that an instruction to end the display is received (step S207: No), the process proceeds to step S206 where the combined data generating circuitry 190 judges whether or not switching between types of blood flow information has been received (step S206). On the contrary, if the combined data generating circuitry 190 has determined that an instruction to end the display is received (step S207: Yes), the combined data displaying process is ended.

As explained above, according to the first embodiment, the extending direction information indicating the blood vessel extending direction is generated, so that the index image data including the extending direction information and the information that indicates the scanned positions by the ultrasound wave transmitted from the ultrasound probe 1 is generated and displayed on the monitor 200. With this arrangement, when the blood flow information is obtained while the blood vessel is scanned so as to obtain the short-axis image, the operator is able to objectively judge whether or not the ultrasound probe 1 is positioned so as to transmit the ultrasound wave onto a perpendicular plane. As a result, when the blood flow information is obtained while the blood vessel is scanned so as to obtain the short-axis image, the operator is able to position the ultrasound probe 1 so as to transmit the ultrasound wave onto the perpendicular plane, the ultrasound diagnosis apparatus is able to obtain accurate blood flow information by varying the transmission direction of the ultrasound beam while in that state.

Further, when the blood flow information is obtained while the blood vessel is scanned so as to obtain the long-axis image, the operator is able to objectively judge whether or not the ultrasound probe 1 is positioned so as to transmit the ultrasound wave to the inside of a plane that is orthogonal to the short axis of the blood vessel and in the direction orthogonal to the blood vessel extending direction. As a result, when the blood flow information is obtained while the blood vessel is scanned so as to obtain the long-axis image, the operator is able to position the ultrasound probe 1 so as to transmit the ultrasound wave to the inside of a plane including the X-axis and in the direction orthogonal to the X-axis. Thus, the ultrasound diagnosis apparatus is able to obtain accurate blood flow information by varying the transmission direction of the ultrasound beam while in that state.

Further, according to the first embodiment, because the pieces of index image data corresponding to the views from the plurality of directions are displayed, it is possible to position the ultrasound probe 1 in a desirable position more accurately.

Further, according to the first embodiment, when the blood flow information is obtained while the blood vessel is scanned so as to obtain the short-axis image, because the index image data is displayed on the monitor 200, the operator is able to easily and precisely recognize the position in which the ultrasound probe 1 is placed so as to transmit the ultrasound wave onto a perpendicular plane. Thus, it is possible to shorten the time required by the medical examination. Similarly, according to the first embodiment, when the blood flow information is obtained while the blood vessel is scanned so as to obtain the long-axis image, because the index image data is displayed on the monitor 200, the operator is able to easily and precisely recognize the position in which the ultrasound probe 1 is placed so as to transmit the ultrasound wave to the inside of a plane that is orthogonal to the short axis of the blood vessel and in the direction orthogonal to the blood vessel extending direction. Thus, it is possible to shorten the time required by the medical examination.

Further, according to the first embodiment, the combined data that schematically expresses the positional relationship among the scanned positions in the blood vessel is generated and displayed on the monitor 200 while being kept in correspondence with the blood flow information at the scanned positions. With this arrangement, the operator is able to, for example, compare the blood flow rates at the scanned positions in the blood vessel with one another, all at once. Further, if the positions of the scanned positions in the combined data are kept in correspondence with the positions thereof in the actual blood vessel, the operator is able to easily detect a stenosis site in the actual blood vessel, by searching for a scanned position having a low blood flow rate.

Exemplary embodiments have thus been explained; however, possible embodiments are not limited to these examples.

OTHER EMBODIMENTS

It is also acceptable to configure the index image data generating circuitry 180 so as to generate index image data that further includes aiding information used for correcting the angle formed by the scanned position by the ultrasound wave transmitted from the ultrasound probe and the extending direction so as to be substantially perpendicular, on the basis of the extending direction information and the information indicating the scanned position. The index image data that further includes the aiding information will be explained, with reference to FIGS. 12A to 14. FIGS. 12A to 14 illustrate examples of index image data corresponding to when a blood vessel long-axis image scan is viewed from the Y-axis direction.

Figure 12A:
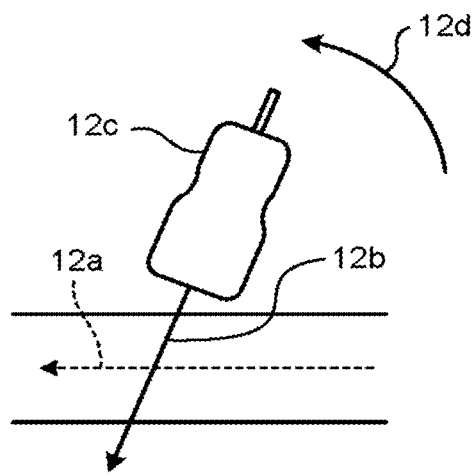
FIG. 12A is a drawing of an example of index image data that further includes aiding information.
Figure 12B:
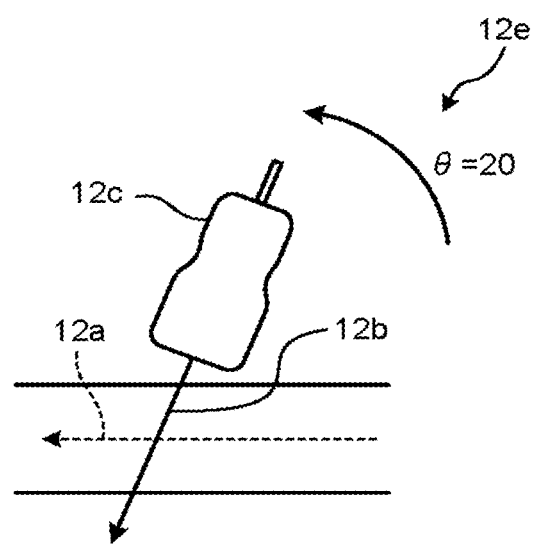
FIG. 12B is a drawing of another example of index image data that further includes aiding information.

FIGS. 12A and 12B are drawings of examples of the index image data that further includes the aiding information. FIGS. 12A and 12B are each a drawing corresponding to when a blood vessel long-axis image scan is viewed from the Y-axis direction. As illustrated in FIG. 12A, the index image data generating circuitry 180 generates index image data including information 12a that indicates the blood vessel extending direction, a center beam 12b, and a schematic drawing of an ultrasound probe 12c. Further, the index image data generating circuitry 180 is configured to arrange the index image data to include aiding information 12d that indicates a direction used for correcting the angle formed by the scanned position by the ultrasound wave transmitted from the ultrasound probe and the extending direction so as to be substantially perpendicular. In the example illustrated in FIG. 12A, the index image data generating circuitry 180 generates the index image data including, as the aiding information 12d, an arrow indicating that the ultrasound probe 1 should be inclined to the left.

Further, it is also acceptable to configure the index image data generating circuitry 180 to arrange the aiding information so as to include the value of the inclination angle. FIG. 12D is a drawing of an example of index image data in which aiding information includes the value of the angle. In the example illustrated in FIG. 12B, the index image data generating circuitry 180 arranges the index image data to include aiding information 12e indicating that the ultrasound probe 1 should be inclined to the left by 20 degrees.

Figure 13A:
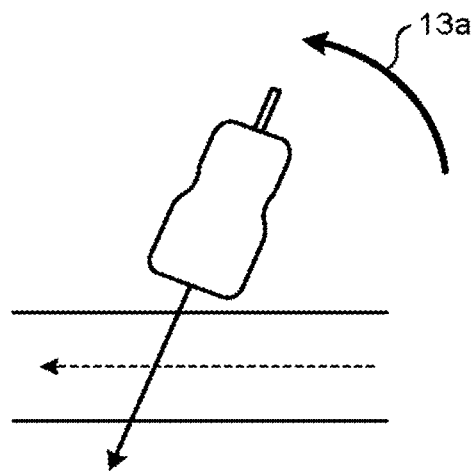
FIG. 13A is a drawing of an example of index image data in which aiding information is varied in accordance with an inclination angle.
Figure 13B:
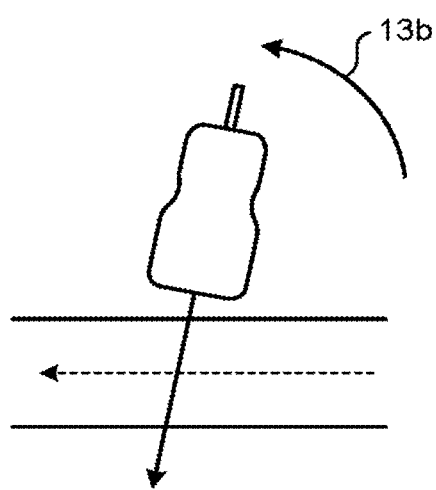
FIG. 13B is another drawing of the example of the index image data in which the aiding information is varied in accordance with the inclination angle.

Further, it is also acceptable to configure the index image data generating circuitry 180 to vary the thickness of the arrow indicating that the ultrasound probe 1 should be inclined, in accordance with the inclination angle. FIGS. 13A and 13B are drawings of examples of index image data in which aiding information is varied in accordance with the inclination angle. The example in FIG. 13A illustrates a situation where the correction angle used for achieving a substantially perpendicular angle is 20 degrees. The example in FIG. 13B illustrates a situation where the correction angle used for achieving a substantially perpendicular angle is 10 degrees. As illustrated in FIGS. 13A and 13B, the index image data generating circuitry 180 changes the thickness of the arrow in aiding information 13a so as to be thinner as illustrated with aiding information 13b, as the value of the correction angle becomes smaller.

Figure 14:
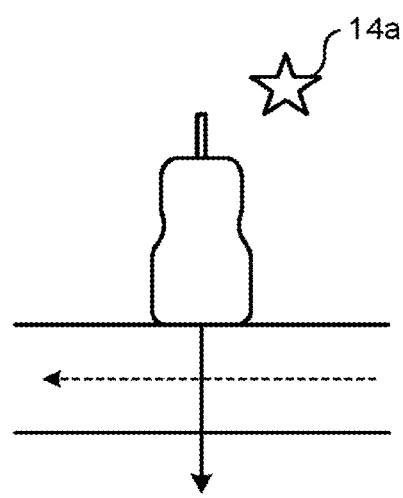
FIG. 14 is a drawing of an example of index image data that includes a notification indicating that it is possible to start obtainment of blood flow information when a substantially perpendicular angle is formed.

Further, it is also acceptable to configure the index image data generating circuitry 180 so as to issue a notification indicating that it is possible to start the obtainment of the blood flow information, if the angle formed by the scanned position by the ultrasound wave transmitted from the ultrasound probe and the extending direction is substantially perpendicular, on the basis of the extending direction information and the information indicating the scanned position. FIG. 14 is a drawing of an example of index image data that includes a notification indicating that it is possible to start the obtainment of the blood flow information when the substantially perpendicular angle is formed. As illustrated in FIG. 14, when the substantially perpendicular angle is formed, the index image data generating circuitry 180 generates index image data that includes, for example, star-shaped aiding information 14a so as to indicate that it is possible to start the obtainment of the blood flow information. The aiding information 14a indicating that it is possible to start the obtainment of the blood flow information does not necessarily have to be star-shaped. Further, the controlling circuitry 170 may arrange the aiding information 14a indicating that it is possible to start the obtainment of the blood flow information so that the display thereof is alternately turned on and off. Alternatively, the controlling circuitry 170 may notify the operator that it is possible to start the obtainment of the blood flow information by outputting voice or an alarm sound.

Figure 15A:
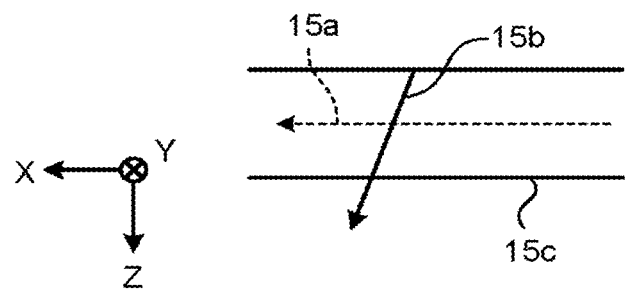
FIG. 15A is a drawing of a modification example of the index image data.
Figure 15B:
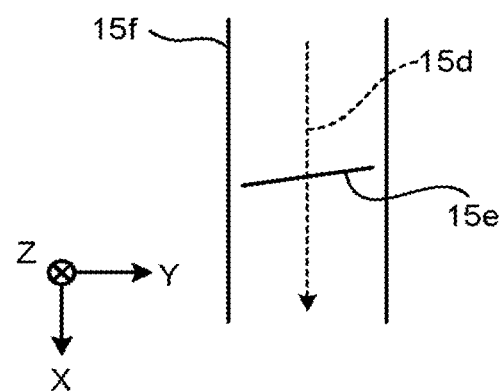
FIG. 15B is a drawing of another modification example of the index image data.
Figure 15C:
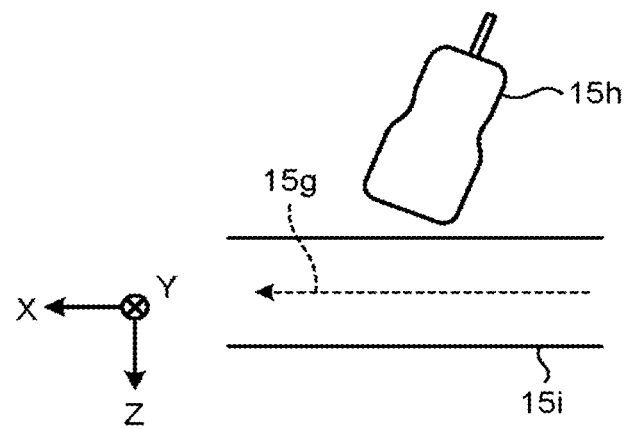
FIG. 15C is a drawing of yet another modification example of the index image data.

Further, as long as the index image data indicates a relative positional relationship between the extending direction and the information indicating the scanned position by the ultrasound wave, the index image data may be altered as appropriate. FIGS. 15A to 15C are drawings of modification examples of index image data. The index image data generating circuitry 180 may generate index image data that does not include a schematic drawing of the ultrasound probe. For example, as illustrated in FIG. 15A, the index image data generating circuitry 180 may generate index image data in which, while no schematic drawing of the ultrasound probe is included, an extending direction 15a and a center beam 15b are superimposed on a schematic drawing of a blood vessel 15c. Alternatively, for example, as illustrated in FIG. 15B, the index image data generating circuitry 180 may generate index image data in which, while no schematic drawing of the ultrasound probe is included, an extending direction 15d and a representative scanned plane 15e are superimposed on a schematic drawing of a blood vessel 15f. Alternatively, the index image data generating circuitry 180 may generate index image data that does not include a center beam or a representative scanned plane. For example, as illustrated in FIG. 15C, the index image data generating circuitry 180 may generate index image data in which, while neither a center beam nor a representative scanned plane is included, an extending direction 15g and a schematic drawing of an ultrasound probe 15h are superimposed on a schematic drawing of a blood vessel 15i. Alternatively, the index image data generating circuitry 180 may generate index image data that does not include a schematic drawing of the blood vessel.

Further, the controlling circuitry 170 may be configured to display one or two of the three pieces of index image data corresponding to the views from the X-axis direction, the Y-axis direction, and the Z-axis direction. For example, when an operation is performed on a short-axis image, the piece of index image data corresponding to the view from the X-axis direction does not necessarily have to be displayed.

Further, the controlling circuitry 170 does not necessarily have to display the three pieces of index image data corresponding to the views from the X-axis direction, the Y-axis direction, and the Z-axis direction, on the monitor 200 at the same time. For example, the controlling circuitry 170 may sequentially display, on the monitor 200, the pieces of index image data each corresponding to a different one of the directions in accordance with selections made by the operator.

Figure 16:
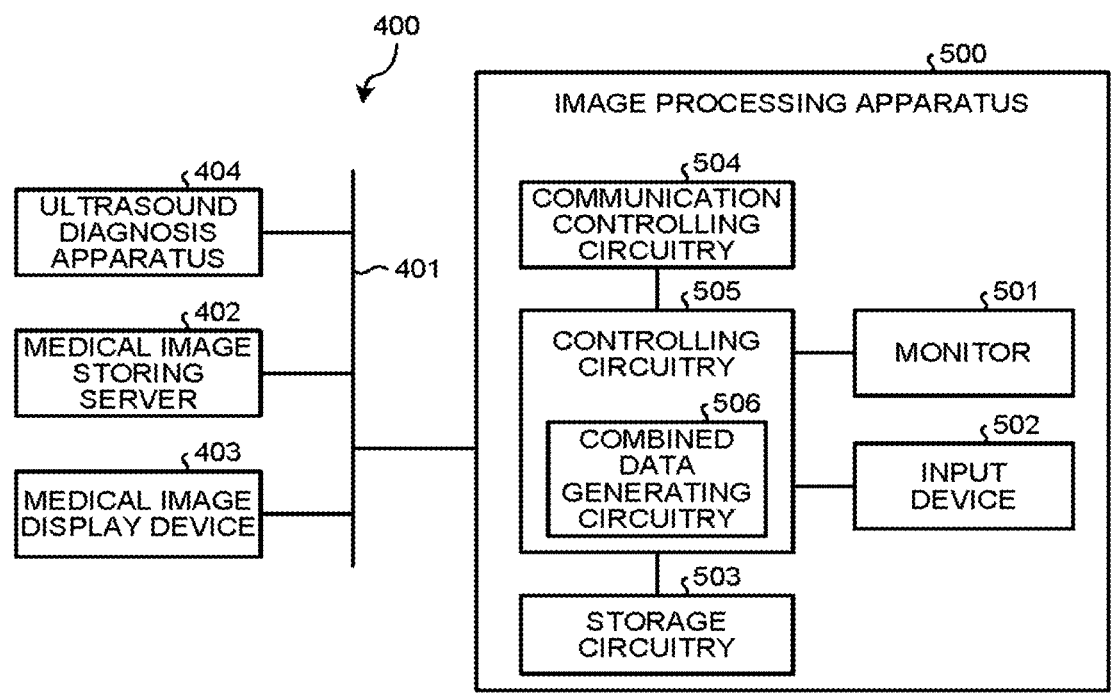
FIG. 16 is a diagram of a medical image processing system that includes an image processing apparatus according to another embodiment.

In the exemplary embodiments above, the example is explained in which the ultrasound diagnosis apparatus includes the combined data generating circuitry 190; however, possible embodiments are not limited to this example. The processes performed by the combined data generating circuitry 190 do not necessarily have to be performed in the ultrasound diagnosis apparatus, and may be performed in an image processing apparatus 500, which is provided in a separate housing. FIG. 16 is a diagram of a medical image processing system 400 that includes the image processing apparatus 500 according to another embodiment. As illustrated in FIG. 16, the medical image processing system 400 includes a medical image storing server 402 compliant with a Picture Archiving and Communication System (PACS), a medical image display device 403, an ultrasound diagnosis apparatus 404, and the image processing apparatus 500. In the medical image processing system 400, the medical image storing server 402, the medical image display device 403, the ultrasound diagnosis apparatus 404, and the image processing apparatus 500 are connected together so as to be able to communicate with one another via a network 401 such as a Local Area Network (LAN). Further, the medical image processing system 400 may include any other modality besides the ultrasound diagnosis apparatus 404.

The medical image storing server 402 is configured to store therein medical image data or the like obtained by the medical image processing system 400. The medical image display device 403 is configured to display the medical image data obtained by the medical image processing system 400. The ultrasound diagnosis apparatus 404 is configured to perform the processes performed by the ultrasound diagnosis apparatus explained in the first embodiment above.

Further, the image processing apparatus 500 includes a monitor 501, an input device 502, storage circuitry 503, communication controlling circuitry 504, and controlling circuitry 505. The monitor 501 is configured to display a GUI used by the operator to input various types of setting requests through the input device 502 and to display ultrasound image data and the like stored in the storage circuitry 503. The input device 502 is configured to receive an input from the operator. The storage circuitry 503 is configured to store therein, for example, information in which a scanned position in a blood vessel is kept in correspondence with blood flow information at the scanned position, as well as volume data generated by the ultrasound diagnosis apparatus 404. The communication controlling circuitry 504 is configured to control data transmissions and receptions to and from the ultrasound diagnosis apparatus 404, the medical image storing server 402, and the medical image display device 403.

The controlling circuitry 505 includes combined data generating circuitry 506. For example, the combined data generating circuitry 506 reads the information in which the scanned position in the blood vessel is kept in correspondence with the blood flow information at the scanned position, from the storage circuitry 503. After that, the combined data generating circuitry 506 generates combined data that indicates a positional relationship between a blood flow information obtainment position and the blood vessel, on the basis of the read information. In this situation, the combined data generating circuitry 506 may be configured not only to obtain the information in which the scanned position in the blood vessel is kept in correspondence with the blood flow information at the scanned position from the ultrasound diagnosis apparatus 404, but also to obtain such information from the medical image storing server 402. Further, the image processing apparatus 500 may be, for example, an image storing device, a medical image display device, or any of various types of devices used in an electronic medical record system.

Further, for example, the volume data or the like that is obtained and generated by the ultrasound diagnosis apparatus is stored into the medical image storing server 402 or is directly sent to the image processing apparatus 500, while having a data structure compliant with, for example, a Digital Imaging and Communications In Medicine (DICOM) standard. In this situation, the data structure does not necessarily have to be one compliant with the DICOM standard, and may be any private data structure.

Further, the processing procedures performed by the index image data generating circuitry 180 and the processing procedures performed by the combined data generating circuitry 190 that are described in the embodiments above can be realized by having a computer execute an "image processing computer program" (hereinafter, "image processing program") stored in the internal storage circuitry 160 in advance. The "image processing program" may be distributed via a network such as the Internet. Further, the "image processing program" may be recorded onto a computer-readable recording medium such as a hard disk, a Flexible Disk (FD), a Compact Disk Read-Only Memory (CD-ROM), a Magneto-Optical (MO) disk, a Digital Versatile Disk (DVD), or the like and may be executed as being read from the recording medium by a computer.

Figure 17:
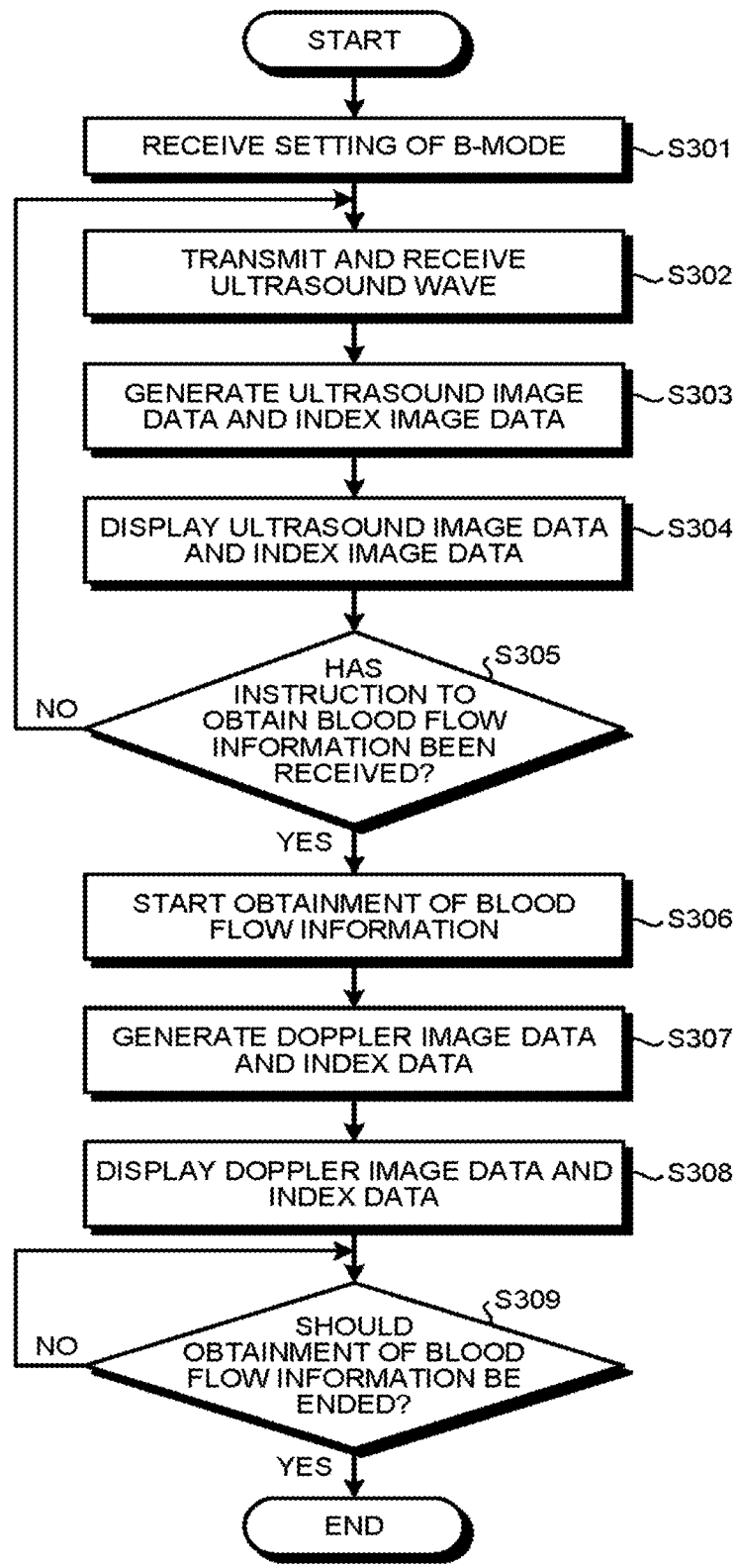
FIG. 17 is a flowchart of an overall processing procedure that is performed when ultrasound images are taken.

Further, in the first embodiment described above, the index image data is sequentially updated and displayed while ultrasound images are taken. A processing procedure performed while the ultrasound images are taken will be explained, with reference to FIG. 17. FIG. 17 is a flowchart of an overall processing procedure that is performed while the ultrasound images are taken.

As illustrated in FIG. 17, the ultrasound diagnosis apparatus receives a setting of the B-mode (step S301). After that, the ultrasound diagnosis apparatus starts transmitting and receiving an ultrasound wave (step S302). Subsequently, the ultrasound diagnosis apparatus generates ultrasound image data and index image data (step S303) and displays the ultrasound image data and the index image data on the monitor 200 (step S304). For example, the ultrasound diagnosis apparatus generates the ultrasound image data by receiving reflected-wave signals, and also, generates the index image data by calculating the blood vessel extending direction while using volume data obtained from the reflected-wave signals. As a result, the operator is able to position the ultrasound probe 1 in a desirable position for starting the obtainment of blood flow information by moving the ultrasound probe 1 while viewing the index image data displayed on the monitor 200.

Further, the ultrasound diagnosis apparatus judges whether or not a freeze button has been pressed and an instruction to obtain blood flow information has been received (step S305). For example, when the operator who viewed the index image data has positioned the ultrasound probe 1 in a desirable position for measuring an accurate blood flow rate, the freeze button is pressed so that the ultrasound diagnosis apparatus receives the instruction to obtain the blood flow information. In this situation, if the ultrasound diagnosis apparatus does not determine that an instruction to obtain the blood flow information is received (step S305: No), the process proceeds to step S302 where the process of generating and displaying the ultrasound image data and the index image data is repeatedly performed until an instruction to obtain the blood flow information is received.

On the contrary, when having determined that an instruction to obtain the blood flow information is received (step S305: Yes), the ultrasound diagnosis apparatus starts the obtainment of the blood flow information (step S306). In that situation, the operator views the index image data, determines that the ultrasound probe 1 is positioned in a desirable position for starting the obtainment of the blood flow information, and starts the obtainment of the blood flow information. After that, the ultrasound diagnosis apparatus freezes the B-mode image and receives, from the operator, a setting for the position of a sample volume used for measuring a blood flow rate in the frozen B-mode image. Further, the ultrasound diagnosis apparatus starts an image taking process in the Doppler mode and measures a blood flow rate. In this situation, the ultrasound diagnosis apparatus measures the blood flow rate by changing the transmission direction of the ultrasound beam, while being positioned in the desirable position for starting the obtainment of the blood flow information. In this situation, when having received the instruction to obtain the blood flow information, the ultrasound diagnosis apparatus alternately performs an image taking process in the B-mode and an image taking process in the pulse Doppler mode at appropriate time intervals.

The ultrasound diagnosis apparatus generates Doppler image data and index image data (step S307) and displays the Doppler image data and the index image data on the monitor 200 (step S308). More specifically, as illustrated in FIG. 8, the ultrasound diagnosis apparatus causes the pulse Doppler image 8a to be displayed on the upper left side of the area of the monitor 200 and causes the frozen B-mode image 8b to be displayed on the upper right side of the area of the monitor 200. Further, the ultrasound diagnosis apparatus causes the index image data 8d corresponding to the view from the Z-axis direction to be displayed on the lower left side of the area of the monitor 200, causes the index image data 8e corresponding to the view from the X-axis direction to be displayed on the lower middle side of the area of the monitor 200, and causes the index image data 8f corresponding to the view from the Y-axis direction to be displayed on the lower right side of the area of the monitor 200.

Further, the ultrasound diagnosis apparatus judges whether an instruction to end the obtainment of the blood flow information has been received (step S309). In this situation, if the ultrasound diagnosis apparatus has determined that an instruction to end the obtainment of the blood flow information is received (step S309: Yes), the process is ended. On the contrary, if the ultrasound diagnosis apparatus does not determine that an instruction to end the obtainment of the blood flow information is received (step S309: No), the judging process at step S309 is repeatedly performed.

Another arrangement is also acceptable in which, if the ultrasound diagnosis apparatus does not determine that an instruction to end the obtainment of the blood flow information is received (step S309: No), the process proceeds to step S307 so that Doppler image data and index image data are each newly generated and displayed. Alternatively, yet another arrangement is also acceptable in which, if the ultrasound diagnosis apparatus does not determine that an instruction to end the obtainment of the blood flow information is received (step S309: No), the process proceeds to step S302 so that an image taking process in the B-mode is performed.

Further, details of the index image data generating process and the displaying process at steps S303 and S304 in FIG. 17 are the same as those in the processing procedure illustrated in FIG. 10. In FIG. 10, from the image memory 150, the index image data generating circuitry 180 obtains, at times, pieces of volume data that are generated at times from reflected-wave signals, calculates the blood vessel extending direction at times, by using the obtained pieces of volume data, and generates pieces of index image data at times. In other words, the index image data generating circuitry 180 calculates the blood vessel extending directions by using the sequentially-generated pieces of volume data, while the image taking process in the B-mode is performed to obtain the ultrasound image data.

In the processing procedures illustrated in FIGS. 10 and 17, the example is explained in which the ultrasound diagnosis apparatus calculates the blood vessel extending direction by using the sequentially-generated pieces of volume data; however, possible embodiments are not limited to this example. For instance, the ultrasound diagnosis apparatus may be configured to calculate the blood vessel extending direction by using volume data obtained from another medical image diagnosis apparatus. In that situation, the ultrasound diagnosis apparatus brings the volume data obtained from the other medical image diagnosis apparatus into association with position information of the ultrasound image data that was taken, by using a magnetic sensor, for example. The ultrasound diagnosis apparatus configured to calculate the blood vessel extending direction by using the volume data obtained from the other medical image diagnosis apparatus will be explained, with reference to FIG. 18.

Figure 18:
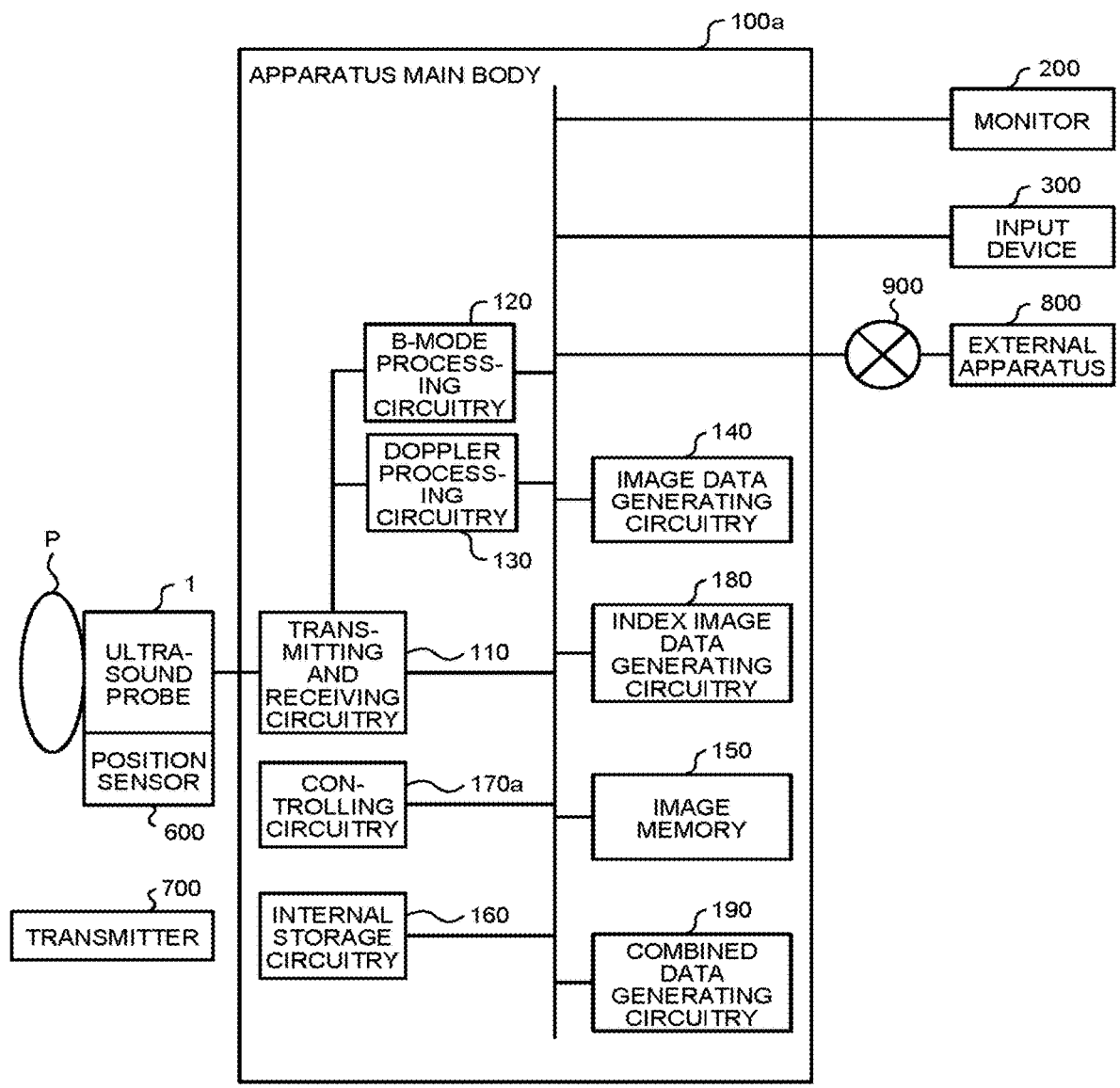
FIG. 18 is a block diagram of an exemplary configuration of an ultrasound diagnosis apparatus according to another embodiment.

FIG. 18 is a block diagram of an exemplary configuration of the ultrasound diagnosis apparatus according to another embodiment. In FIG. 18, some of the constituent elements that are the same as those in the ultrasound diagnosis apparatus illustrated in FIG. 1 will be referred to by using the same reference characters, and detailed explanation thereof will be omitted. As illustrated in FIG. 18, the ultrasound diagnosis apparatus according to said another embodiment includes the ultrasound probe 1, an apparatus main body 100a, the monitor 200, the input device 300, a position sensor 600, and a transmitter 700. Further, the apparatus main body 100 is connected to an external apparatus 800 via a network 900.

The position sensor 600 and the transmitter 700 are devices used for obtaining position information of the ultrasound probe 1. For example, the position sensor 600 is a magnetic sensor attached to the ultrasound probe 1. Further, for example, the transmitter 700 is a device disposed in an arbitrary position and configured to form a magnetic field that is centered thereon and extends outwardly.

The position sensor 600 detects the three-dimensional magnetic field formed by the transmitter 700. After that, the position sensor 600 calculates the position (the coordinates and the angle) thereof in a space that uses the transmitter 700 as the origin on the basis of the information about the detected magnetic field and transmits the calculated position to controlling circuitry 170a (explained later). In this situation, the position sensor 600 transmits the three-dimensional coordinates of the position of its own and the angle thereof to the controlling circuitry 170a (explained later), as three-dimensional position information of the ultrasound probe 1.

The external apparatus 800 is an apparatus connected to the apparatus main body 100a. For example, the external apparatus 800 may be any of various types of medical image diagnosis apparatuses other than the ultrasound diagnosis apparatus of the present embodiment, such as a database in a Picture Archiving and Communication System (PACS) that is a system used for managing various types of medical image data, an X-ray Computed Tomography (CT) apparatus, a Magnetic Resonance Imaging (MRI) apparatus, or the like.

As illustrated in FIG. 18, the apparatus main body 100a includes the transmitting and receiving circuitry 110, the B-mode processing circuitry 120, the Doppler processing circuitry 130, the image data generating circuitry 140, the image memory 150, the internal storage circuitry 160, the controlling circuitry 170a, the index image data generating circuitry 180, and the combined data generating circuitry 190. The internal storage circuitry 160 is configured to store therein data transferred thereto from the external apparatus 800 via an interface (not illustrated). For example, the internal storage circuitry 160 stores therein a Computed Tomography (CT) image taken by an X-ray CT apparatus.

The controlling circuitry 170a is configured to bring volume data obtained from another medical image diagnosis apparatus into association with position information of the ultrasound image data that was taken, by using the three-dimensional position information of the ultrasound probe 1 obtained from the position sensor 600. In the following sections, an example will be explained in which the CT image taken by the X-ray CT apparatus is used as the volume data obtained from another medical image diagnosis apparatus.

First, before performing an ultrasound examination on the subject P by using the ultrasound probe 1, the controlling circuitry 170a requests the internal storage circuitry 160 to transfer X-ray CT volume data obtained by taking images of an image taking site (an examined site) of the subject P, in accordance with an instruction from the operator. In this situation, the X-ray CT volume data may be, for example, data obtained by taking images of a three-dimensional region that includes the image taking site of the subject P and may be, for example, constituted with pieces of X-ray CT image data representing 500 images taken on axial planes. The controlling circuitry 170a displays one of the pieces of X-ray CT image data representing one of the plurality of axial-plane images, on the monitor 200. In this situation, the monitor 200 divides the display area thereof into sections as illustrated in FIG. 8 and displays the piece of X-ray CT image data in the display area on the upper left side.

Subsequently, the controlling circuitry 170a aligns the three axes of the X-ray CT volume data with the three axes of the coordinate system of the scanned cross-sectional plane of the ultrasound probe 1. In that situation, for example, the operator causes the ultrasound probe 1 to perpendicularly abut against the body surface of the subject P, so as to scan an axial plane at the image taking site of the subject P and presses a set button included in the input device 300. At the point in time when the button is pressed, the controlling circuitry 170a obtains the three-dimensional position information of the ultrasound probe 1 obtained from the position sensor 600, as initial position information. Also, at the point in time when the set button is pressed, the monitor 200 displays ultrasound image data generated by the image data generating circuitry 140. In this situation, the monitor 200 display the ultrasound image data in the display area on the upper right side, which is one of the divided sections as illustrated in FIG. 8. As a result, the monitor 200 displays the X-ray CT image on the upper left side of the display area and displays the ultrasound image data on the upper right side of the display area.

The operator operates a mouse or the like included in the input device 300, for example, so that a piece of X-ray CT image data corresponding to substantially the same cross-sectional plane as that of the ultrasound image data is displayed on the monitor 200. Further, at the point in time when the piece of X-ray CT image data corresponding to the cross-sectional plane (the axial plane) that is substantially the same as that of the ultrasound image data is displayed, the operator presses the set button again. As a result, from the X-ray CT volume data, the controlling circuitry 170a obtains the position of the cross-section plane that is substantially the same as the scanned cross-sectional plane of the ultrasound probe 1 indicated by the initial position information. At this stage, even if the position of the ultrasound probe 1 is moved by the operator, the controlling circuitry 170a is able to identify the same cross-sectional plane as the scanned cross-sectional plane of the ultrasound probe 1 from the X-ray CT volume data, on the basis of the three-dimensional position information of the ultrasound probe 1 obtained from the position sensor 600.

Subsequently, by matching a feature point in the ultrasound image data with a feature point in the X-ray CT image data to form at least one pair, the controlling circuitry 170a aligns the positions between the ultrasound image data and the X-ray CT image data. For example, the operator specifies the xiphoid process as the feature point that corresponds between the X-ray CT image data and the ultrasound image data. The controlling circuitry 170a further calculates a transformation matrix for transforming coordinates of each of the points in the ultrasound image data into coordinates of a corresponding point in the X-ray Ct image data (X-ray CT volume data), by using the position of the feature point specified from the X-ray CT image data and the position of the feature point specified from the ultrasound image data. As a result, even if the position of the ultrasound probe 1 is moved by the operator, the controlling circuitry 170a is able to identify the same cross-sectional plane as the scanned cross-sectional plane of the ultrasound probe 1 from the X-ray CT volume data on the basis of the three-dimensional position information of the ultrasound probe 1 obtained from the position sensor 600 and is further able to calculate the coordinates on the identified cross-sectional plane corresponding to any of the coordinates in the ultrasound image data generated from the scan performed by the ultrasound probe 1, by using the transformation matrix.

The controlling circuitry 170a notifies the image data generating circuitry 140 of position alignment information obtained by using the transformation matrix. By using the position alignment information, the image data generating circuitry 140 generates, from the X-ray CT volume data, X-ray CT image data (MPR image data) of which the position is aligned with the ultrasound image data that has been scanned and generated at the current point in time.

Subsequently, when blood flow information is to be obtained, to judge whether the ultrasound probe 1 is positioned in a desirable position for starting the obtainment of the blood flow information, the operator issues an instruction to start displaying index image data. In that situation, for example, as illustrated in FIG. 8, the index image data generating circuitry 180 causes index image data 8d corresponding to a view from the Z-axis direction to be displayed on the lower left side of the area of the monitor 200, causes index image data 8e corresponding to a view from the X-axis direction to be displayed on the lower middle side of the area of the monitor 200, and causes index image data Of corresponding to a view from the Y-axis to be displayed on the lower right side of the area of the monitor 200. In this situation, the index image data generating circuitry 180 identifies the X-ray CT image data that matches the ultrasound image data, extracts a blood vessel region from the X-ray CT volume data containing the X-ray CT image data, and calculates the blood vessel extending direction. Further, the index image data generating circuitry 180 generates index image data in which information indicating the scanned position by the ultrasound wave transmitted from the ultrasound probe 1 and the blood vessel extending direction are superimposed on a schematic drawing of the blood vessel. The index image data generating circuitry 180 causes the generated index image data to be displayed in a lower section of the area of the monitor 200. As a result, by viewing the index image data, the operator is able to judge whether the ultrasound probe 1 is positioned in a desirable position for staring the obtainment of the blood flow information.

By using the ultrasound diagnosis apparatus and the controlling method according to at least one aspect of the embodiments described above, it is possible to accurately measure the blood flow rate and to improve the precision level of the ultrasound diagnosis.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:
1. An ultrasound diagnosis apparatus, comprising:
index image data generating circuitry configured to generate index image data indicating a relative positional relationship between extending direction information and information indicating a scanned position by an ultrasound wave transmitted from an ultrasound probe, wherein the extending direction information indicates a blood vessel extending direction and is generated based on volume data representing a three-dimensional region that includes at least a part of the blood vessel region of a subject;
blood flow data generating circuitry configured to generate blood flow data that indicates a positional relationship between a blood flow information obtainment position and a blood vessel; and
controlling circuitry configured to cause a monitor to display the index image data and the blood flow data,
wherein the blood flow data generating circuitry is further configured to generate the blood flow data by positioning a partition, in a schematic drawing of the blood vessel that is in a shape of a circular cylinder, and incline the partition based on angle information about the relative positional relationship and when the ultrasound wave transmitted from the ultrasound probe is perpendicular to the blood vessel extending direction, the partition is rendered as a perfect circle and when the ultrasound wave transmitted from the ultrasound probe is not perpendicular to the blood vessel extending direction, the partition is rendered as an oval.

2. The ultrasound diagnosis apparatus according to claim 1, further comprising image data generating circuitry configured to generate the volume data by performing a scan using the ultrasound wave transmitted from the ultrasound probe, wherein the index image data generating circuitry sequentially generates pieces of the extending direction information, each of which indicates a blood vessel extending direction in a three-dimensional space based on pieces of the volume data that are sequentially generated by the image data generating circuitry, and sequentially generates pieces of the index image data, each of which indicates a relative positional relationship between a different one of the generated pieces of extending direction information and the information indicating the scanned position.

3. The ultrasound diagnosis apparatus according to claim 2, wherein the index image data generating circuitry is further configured to generate the index image data further including aiding information used for correcting an angle formed by the scanned position by the ultrasound wave transmitted from the ultrasound probe and the extending direction so as to be perpendicular, based on the extending direction information and the information indicating the scanned position.

4. The ultrasound diagnosis apparatus according to claim 1, further comprising: a position sensor configured to obtain position information of the ultrasound probe, wherein the index image data generating circuitry is further configured to generate the extending direction information indicating the blood vessel extending direction in a three-dimensional space from a piece of volume data that was obtained in a past and of which a position is aligned with that of a piece of ultrasound image data currently being scanned based on the position information of the ultrasound probe, and generates the index image data indicating the relative positional relationship between the generated extending direction information and the information indicating the scanned position.

5. The ultrasound diagnosis apparatus according to claim 4, wherein the index image data generating circuitry is further configured to generate the index image data further including aiding information used for correcting an angle formed by the scanned position by the ultrasound wave transmitted from the ultrasound probe and the extending direction so as to be perpendicular, based on the extending direction information and the information indicating the scanned position.

6. The ultrasound diagnosis apparatus according to claim 1, wherein the index image data generating circuitry is further configured to generate the index image data further including aiding information used for correcting an angle formed by the scanned position by the ultrasound wave transmitted from the ultrasound probe and the extending direction so as to be perpendicular, based on the extending direction information and the information indicating the scanned position.

7. The ultrasound diagnosis apparatus according to claim 1, wherein the index image data generating circuitry is further configured to issue a notification about obtaining blood flow information, when an angle formed by the scanned position by the ultrasound wave transmitted from the ultrasound probe and the extending direction is perpendicular, based on the extending direction information and the information indicating the scanned position.

8. The ultrasound diagnosis apparatus according to claim 1, wherein the controlling circuitry is further configured to display the index image data in a part of a display area of the monitor.

9. The ultrasound diagnosis apparatus according to claim 1, wherein the information indicating the scanned position includes at least one of the following: information indicating a representative scanned plane that is a scanned plane positioned at a center among a plurality of two-dimensional scanned planes, and information indicating such an ultrasound beam that is transmitted from a center of the ultrasound probe among a plurality of ultrasound beams transmitted to an inside of the representative scanned plane.

10. The ultrasound diagnosis apparatus according to claim 9, wherein the information indicating the scanned position further includes information that schematically indicates a position of the ultrasound probe.

11. The ultrasound diagnosis apparatus according to claim 1, wherein the partition corresponds to a measuring position and is colored in accordance with a blood flow rate value at the corresponding measuring position.

12. The ultrasound diagnosis apparatus according to claim 11, wherein, when having received a selection of a measuring position, the controlling circuitry is configured to cause the monitor to display blood flow data kept in correspondence with the selected measuring position.

13. The ultrasound diagnosis apparatus according to claim 1, wherein, when having received a selection of a measuring position, the controlling circuitry is configured to cause the monitor to display blood flow data kept in correspondence with the selected measuring position.

14. The ultrasound diagnosis apparatus according to claim 1, wherein, when having received a selection of a measuring position, the controlling circuitry is configured to cause the monitor to display blood flow data kept in correspondence with the selected measuring position.

15. The ultrasound diagnosis apparatus according to claim 1, wherein the blood flow data includes blood flow rate information.

16. A controlling method executed by an ultrasound diagnosis apparatus, the controlling method comprising:

generating index image data indicating a relative positional relationship between extending direction information and information indicating a scanned position by an ultrasound wave transmitted from an ultrasound probe, wherein the extending direction information indicates a blood vessel extending direction and is generated based on volume data representing a three-dimensional region that includes at least a part of the blood vessel region of a subject;

generating blood flow data that indicates a positional relationship between a blood flow information obtainment position and a blood vessel;

causing a monitor to display the index image data and the blood flow data;

generating the blood flow data by positioning a partition, in a schematic drawing of the blood vessel that is in a shape of a circular cylinder;

when the ultrasound wave transmitted from the ultrasound probe is perpendicular to the blood vessel extending direction, rendering the partition as a perfect circle and when the ultrasound wave transmitted from the ultrasound probe is not perpendicular to the blood vessel extending direction, rendering the partition as an oval; and inclining the partition based on angle information about the relative positional relationship.

17. The method according to claim 16, further comprising:
  generating the volume data by performing a scan using the ultrasound wave transmitted from the ultrasound probe,
  wherein the generating index image data further comprises
    sequentially generating pieces of the extending direction information, each of which indicates a blood vessel extending direction in a three-dimensional space based on pieces of the volume data that are sequentially generated by the image data generating circuitry, and
    sequentially generating pieces of the index image data, each of which indicates a relative positional relationship between a different one of the generated pieces of extending direction information and the information indicating the scanned position.

18. The method according to claim 16, further comprising:
  obtaining position information from a position sensor of the ultrasound probe,
  wherein the generating index image data further comprises:
    generating the extending direction information indicating the blood vessel extending direction in a three-dimensional space from a piece of volume data that was obtained in a past and of which a position is aligned with that of a piece of ultrasound image data currently being scanned based on the position information of the ultrasound probe, and
    generating the index image data indicating the relative positional relationship between the generated extending direction information and the information indicating the scanned position.

19. The method according to claim 16, wherein the generating index image data further comprises:
  generating the index image data to further include aiding information used for correcting an angle formed by the scanned position by the ultrasound wave transmitted from the ultrasound probe and the extending direction so as to be perpendicular, based on the extending direction information and the information indicating the scanned position.

* * * * *